United States Patent [19]
LaMotte, III

[11] Patent Number: 5,296,347
[45] Date of Patent: Mar. 22, 1994

[54] BRIDGE IMMUNOASSAY

[75] Inventor: George B. LaMotte, III, Larkspur, Calif.

[73] Assignee: Ciba Corning Diagnostics Corp., Medfield, Mass.

[21] Appl. No.: 14,092

[22] Filed: Feb. 4, 1993

Related U.S. Application Data

[63] Continuation of Ser. No. 653,024, Feb. 8, 1991, abandoned.

[51] Int. Cl.$^5$ .............. G01N 33/569; G01N 33/543; G01N 33/53; G01N 33/536
[52] U.S. Cl. ........................... 435/5; 435/7.1; 435/7.5; 435/7.9; 435/7.92; 435/7.93; 435/7.94; 435/7.95; 435/961; 435/971; 436/501; 436/536; 436/538; 436/540
[58] Field of Search .................. 435/7.5; 436/501

[56] References Cited

U.S. PATENT DOCUMENTS 4,299,916 11/1981 Litman et al. ........................... 435/6
4,808,521 2/1989 Allen ................... 435/7.93

Primary Examiner—Christine M. Nucker
Assistant Examiner—Chris Dubrule
Attorney, Agent, or Firm—Leona L. Lauder; Arthur S. Morgenstern; Norman J. Kruse

[57] ABSTRACT

Disclosed is a novel immunoassay methodology, bridge immunoassay, which employs a primary free solution analyte/receptor binding reaction, for example, in a sandwich-type format (two or more analyte receptors), in a competitive format (single analyte receptor) or in a related immunoassay format, and a universal solid phase and capture system. The universal capture system comprises a first receptor bound to a solid phase and a bridge receptor (a second receptor) which functions both as a ligand for said bound first receptor and as a receptor for a ligand conjugated to a sample analyte receptor (a third receptor). The bridge receptor is used to immobilize the immunocomplexes formed free in solution by linking them to the bound first receptor. The universal capture system can be used for assays for any analyte as the bridge receptor binds to a ligand, for example, a hapten or binding protein, conjugated to the sample analyte receptor. Methods, compositions and test kits for such bridge immunoassays are provided.

41 Claims, 8 Drawing Sheets

BRIDGE IMMUNOASSAY

This is a continuation of copending application(s) Ser. No. 07/653,024 filed on Feb. 8, 1991, abandoned.

FIELD OF THE INVENTION

This invention is in the field of immunoassays relating to compositions and methods for detecting and/or determining the concentration of analytes in fluids, such as serum or tissue extracts. Specifically, the invention relates to a novel immunoassay methodology wherein a universal capture system is employed. More specifically, the invention relates to such an immunoassay capture system wherein an immunocomplex containing the sample analyte is formed in solution and then captured and insolubilized by a universal bridge receptor which links the immunocomplex to a solid phase through a first receptor thereto.

BACKGROUND

The present invention relates to methods and compositions for immunoassays, and to kits for carrying out such methods and containing such compositions. The invention more specifically relates to immunoassays in which at least three receptors are employed to capture and insolubilize a sample analyte.

Receptors are generally proteins, although other substances having reversible specific binding affinity for a ligand or for a labeled analogue thereof are equally useful. The most commonly used receptors are antibodies because they can be raised to bind any desired ligand. However, other binding proteins are included within the meaning of receptor, for example, avidin, streptavidin, lectins, enzymes, apoenzymes, hydrophobic protein binding sites, intrinsic factor, thyroxine binding globulin, cortisol binding protein, folate binding protein, and membrane-associated specific receptor proteins. Receptors may also include polynucleic acid sequences and low molecular weight substances, such as, dyes or biotin. As a general rule, receptors are the larger of the two components of a binding pair. However, for the purposes of the present invention, a receptor is to be construed as simply one component of a binding pair.

Ligands are the converse of receptors. Whereas ligands are ordinarily low molecular weight organic compounds, they are defined for purposes of this invention, as one component of a binding pair, a receptor being the other component, wherein the ligand may be larger or smaller than the receptor.

Labeled ligand analogues are derivatives of ligands which carry a detectable substituent, such as, an enzyme, radioisotope, stable free radical or other known label, but which are recognizable by and bind to a receptor for the parent ligand (sample analyte) with approximately the same affinity as exhibited by the parent ligand.

A ligand-receptor pair is by definition reversibly bindable, that is, its behavior is governed by the law of mass action. On a practical level, "reversibly bindable" indicates that either component of the ligand-receptor pair is displaceable by structurally related substances under the conditions normally encountered in immunoassays, that is, mild pH and temperature, and moderate ionic strength.

Immunoassays employing double receptors are known in the art. Such double receptor immunoassays have as their salient feature a first receptor specific for a second receptor wherein the second receptor ordinarily binds to the ligand (analyte) which is the substance which is to be determined in the assay. Exemplary of such a double receptor immunoassay is that disclosed in U.S. Pat. No. 4,343,896 (issued Aug. 10, 1982 to Wolters and Kuypers) wherein a sandwich immunocomplex is noncovalently bonded to a solid phase through immobilized polyclonal antibodies raised against one of the antibodies of the sandwich.

The double receptor methods (without the use of binding ligands) have a number of disadvantages, principally because the affinity of such receptors for one another is not sufficiently high. Such limitations are manifested in requirements for relatively large plastic or solid surfaces for adsorption of receptor, making it difficult to use such a format in a coated tube, and for prolonged incubations. The low affinities are critical when the receptor or the antigen used to raise the receptor for the sample ligand is difficult to obtain.

U.S. Pat. No. 4,271,140 (issued Jun. 2, 1981 to Bunting) provides one method of overcoming such nonspecificity of one receptor for another in a double receptor immunoassay context. That patent is based on the fact that the affinity of antibodies for binding ligands is high. (Wilchek et al., *FEBS Letters.*, 31(1):149-152 (April, 1973); Abbas et al., *J. Immunol*, 11 4(4):1197-1204 (April 1975); Lamm et al., *PNAS* (USA), 69(12):3732-3736 (December, 1972); and Wofsy et al., *J. Exp. Med.*, 140:523-537 (1974) ) The Bunting patent claims an improvement to double receptor specific binding assays wherein instead of a double receptor, the assay comprises a receptor complex having a binding ligand (BL), a labeled or unlabeled receptor specific for the binding ligand ($A_{BL}$) and a second receptor ($A_1$). The configuration of the complex is $A_{BL}$ (BL)n $A_1$ (wherein n is at least one), and BL is reversibly bound to $A_{BL}$ and covalently bound to $A_1$. BL can be fluorescein isothiocyanate (FITC).

Another patent employing the concept of using a binding ligand, termed therein a hapten, to increase the specificity of one receptor for another in double receptor immunoassays is U.S. Pat. No. 4,659,678 (issued to Forrest et al. on Apr. 21, 1987). That patent claims an immunoassay method for an antigen comprising incubating a mixture of: (a) a liquid sample; (b) labeled monoclonal antibodies to the antigen; (c) monoclonal antibodies to the antigen which are conjugated with a hapten; and (d) an antibody raised to the hapten which non-covalently bonds to the hapten and which is bound to a solid phase support. The hapten can be fluorescein isothiocyanate. That patent further discloses at column 5, lines 14-18, an immunoassay method wherein a specific binding protein and its corresponding ligand, for example, avidin and biotin, are respectively bound to a solid phase and conjugated to an antibody to the antigen under assay and by the noncovalent bonding thereof effect the insolubilization of an immunocomplex of the antigen, a labeled antibody thereto, and the unlabeled antibody conjugated to the ligand of the specific binding pair.

Other exemplary variations of the double receptor immunoassay include the following three references.

European Patent Application Publication No. 337,082 (assigned to BioRad Lab. Inc.) describes an immunoassay wherein an anti-biotin antibody is immobilized on a solid support and incubated with a biotinylated binding species, which is able to bind a sample ligand, so as to produce a ligand-specific binding site on the support.

European Patent Application Publication No. 344,578 (assigned to Boehringer Mannheim GMBH) describes a heterogeneous immunoassay using a solid phase to which an immunological reactant is fixed wherein the new feature is that the solid phase used is a reaction vessel having fixed to its internal surfaces enough streptavidin or avidin to provide 0.1 to 2.5 micrograms/milliliter ($\mu$tg/ml) of reaction volume. The reaction vessels are described as being useful for any assay in which the antibody or antigen which is to be immobilized can be conjugated with biotin.

U.S. Pat. No. 4,778,751 (issued to El Shami et al. on Oct. 18, 1988) claims a method for measuring the level of an analyte (an antigen, antibody or hapten) in a liquid sample which sequentially comprises: (a) forming a soluble complex wherein the analyte is linked through a specific antibody, antigen or anti-hapten depending on the analyte, to a soluble matrix which carries a ligand (X) and is capable of being chemically attached to more than one specific antibody, antigen or antihapten; (b) forming an insolubilized complex comprising a solid support linked to the ligand (X) of the matrix through an anti-ligand (Y) wherein the insolubilized complex carries a label (Z) linked to the analyte through an anti-antigen, anti-antibody or anti-hapten; (c) washing the insolubilized complex; and (d) observing the presence of label. The ligand (X) can be biotin; and the anti-ligand (Y) can be avidin. The soluble matrix can be a soluble carbohydrate, dextran or a soluble polymer.

The El Shami et al. patent further discloses at column 21, lines 34–68 and column 22, lines 1–5, variations of said method wherein it is desired to capture the analyte in a liquid phase and then immobilize the soluble matrix in the same reaction. Three possible configurations are disclosed as follows: (1) X and Y are both avidin; and biotin is added after the initial liquid phase reaction has been completed; (2) X is biotin, Y is antiavidin and avidin is added after the liquid phase reaction; and (3) X is biotin, Y is a biotinylated protein, and avidin is added after the liquid phase reaction.

The novel immunoassay system of the present invention provides a capture system comprising at least three receptors. The first two receptors constitute a generic capture system applicable to a variety of immunoassay formats for any analyte. The first receptor is bound to a solid phase and has as its ligand a second receptor or a ligand conjugated to said second receptor, wherein said second receptor is a bridge receptor, preferably an anti-hapten bridge receptor. The second receptor is termed a bridge receptor in that it provides a bridge between an immunocomplex formed freely in solution and the first receptor bound to the solid phase. The bridge receptor therefore separates the immunocomplex containing the analyte under assay from the liquid phase. The bridge receptor binds to a ligand conjugated to a sample analyte receptor, the third receptor. The third receptor has as its ligand either the analyte under assay or a further receptor which has as its ligand the analyte under assay.

It is an object of the present invention to provide a novel immunoassay methodology which not only overcomes the problem of nonspecificity of the noncovalent bonding between receptors of prior art double receptor immunoassays but also provides for the advantages of liquid phase kinetics and lack of steric hindrance in forming an immunocomplex.

It is further an object of the present invention to provide a universal solid phase and capture system which can be employed for competitive, sandwich, competitive/sandwich and related immunoassays for any analyte.

It is a further object of this invention to provide for a generic capture system, which is stable, has a long shelf life, and provides a solid phase component which has a first receptor uniformly bound to it. The generic capture system provides a solid phase coated with a first receptor, such as avidin or streptavidin, and a bridge receptor, such as a biotinylated anti-hapten antibody, which can be used irrespective of the analyte under assay.

It is a still further object of the invention to provide a solid phase uniformly coated with the first receptor that can be used with a variety of bridge receptors, for example, a variety of biotinylated antibodies raised against different haptens. Thus, if, for example, there is a concern that a particular hapten might represent a cross-reactivity problem when a particular analyte is to be assayed, a more preferred bridge receptor raised against a different hapten can be selected.

In preferred embodiments of this invention, options are provided wherein it is unnecessary to immobilize antibodies to the solid phase, for example, wherein avidin or more preferably streptavidin is the first receptor, and a very uniform, stable and consistent coating of the solid phase can be produced.

It is still further an object of the invention to provide for an immunocomplex capture step that can be driven to rapid completion by optimizing the amount of a generic bridge receptor that is added to the reaction mixture, preferably after the immunocomplex has been formed in solution.

Other objects of this invention will be apparent to those skilled in the art from a consideration of this specification and attached claims taken in their entirety.

SUMMARY OF THE INVENTION

The present invention concerns a novel immunoassay methodology wherein at least three receptors are used to capture and immobilize an analyte in a fluid sample. The first and second receptors provide a generic capture system wherein the first receptor is bound to a solid phase and has as its ligand a second receptor or a ligand conjugated to said second receptor, wherein said second receptor is termed herein a bridge receptor. The bridge receptor is a receptor which has as its ligand, a ligand conjugated to a third receptor, a sample analyte receptor. Preferably, said ligand is a hapten or a member of a specific binding pair, such as, avidin or streptavidin and biotin, more preferably a hapten. The third receptor, sample analyte receptor, has as its ligand either the analyte which is to be detected or quantified in the fluid sample, or a receptor to said analyte. The analyte can be an antigen, antibody or hapten. Thus, as there are at least three receptors used to capture the analyte and immobilize the immunocomplexed analyte, the immunoassay methodology of this invention can be termed a triple receptor (or triple ligand) assay. Alternatively and preferably, the immunoassay methodology of this invention can be termed a bridge immunoassay system.

The bridge receptor (second receptor) and third receptor (sample analyte receptor) are essentially each a ligand/receptor combination in that they are conjugates of a ligand and a receptor. For example, in preferred embodiments of the invention, the bridge receptor can be a biotinylated anti-FITC antibody wherein the biotin thereon is a ligand for the first receptor, avidin or streptavidin in such preferred embodiments, and a receptor for the hapten FITC which is conjugated to the third receptor; the third receptor in such preferred embodiments is an FITC-conjugated anti-analyte antibody wherein the conjugated FITC is a ligand for the anti-FITC bridge receptor, and the antibody portion is a receptor for the analyte under assay. Similarly, other ligand/receptor combinations for the bridge receptor include anti-hapten antibodies conjugated to a member of a specific binding pair, such as, avidin or streptavidin and biotin, wherein the first receptor is a hapten and the third receptor is an anti-analyte antibody conjugated to the other member of the specific binding pair. Further ligand/receptor combinations for the bridge receptor include haptens conjugated to a member of a specific binding pair, such as, avidin or streptavidin and biotin, wherein the first receptor is an anti-hapten antibody and the third receptor is an anti-analyte antibody conjugated to the other member of the specific binding pair.

The immunoassay methodology of this invention can be used in any standard immunoassay format. In a sandwich immunoassay format, a labeled fourth receptor, in this case to the sample analyte, is used to form a sandwich immunocomplex in solution with the analyte and the third receptor. After the initial liquid phase reaction, the bridge receptor (second receptor) is added to the liquid sample where it binds to a ligand conjugated to the sample analyte receptor (third receptor) and pulls the immunocomplex out of solution by binding to the first receptor, which is bound to the solid phase. The amount of label (on the fourth receptor) immobilized upon the solid phase or remaining in the liquid phase can then be measured by conventional means to detect whether or not the analyte had been present in the sample and if so, determine the amount of analyte that had been present.

FIG. 1A-B provides a schematic of a preferred embodiment of a bridge sandwich immunoassay format of this invention. In that preferred embodiment, the first receptor is avidin; the second receptor is a biotinylated bridge polyclonal antibody which was raised to the hapten fluorescein isothiocyanate (FITC); the third receptor is a monoclonal antibody to the sample analyte, an antigen, to which the hapten fluorescein isothiocyanate (FITC) is conjugated; and the fourth receptor is an enzyme-labeled monoclonal antibody to the sample antigen. (In further preferred embodiments, the bridge receptor is a monoclonal antibody.) In the embodiment of FIG. 1, an enzymatic label is used; after the immunocomplex is immobilized to the solid phase, the excess reagent and sample are washed away, and the substrate for the enzyme is added. After an incubation period for color development or formation of the end product of the enzymatic reaction, the color can be read spectrophotometrically or by other conventional means, or the amount of enzymatic end product can be determined, resulting in a proportional measure of the amount of analyte that had been present in the sample.

In a competitive immunoassay format, a labeled version of the sample analyte, this is, a labeled analyte analogue, is used. In that format there is an initial liquid phase reaction wherein the sample, the labeled analyte analogue, and third receptor (preferably a hapten conjugated sample analyte receptor) are mixed and incubated to form immunocomplexes comprising the third receptor and either the sample analyte or the labeled analyte analogue. Then the bridge receptor (second receptor) is added to the sample and during a second incubation period binds both to the third receptor, more specifically to a ligand conjugated to the third receptor, and to the first receptor attached to the solid phase. As in the sandwich immunoassay, a preferred embodiment of the competitive immunoassay system of this invention comprises that wherein the first receptor is avidin, still more preferably streptavidin; wherein the bridge receptor is a biotinylated polyclonal or monoclonal antibody, more preferably a monoclonal antibody, that has been preferably raised against a hapten, and more preferably raised against FITC, and wherein the third receptor is an antibody, preferably monoclonal, to the sample analyte and is conjugated to the hapten against which the bridge antibody was raised, preferably to FITC. The label on the analyte analogue can be any label conventionally used, and in a preferred embodiment is in enzymatic label. As in the sandwich immunoassay of this invention, wherein the label is enzymatic, after the second incubation, the unbound reactants are washed away and the substrate for the enzyme is added and incubated with the bound immunocomplexes. Color development is then read or the amount of end product of the enzymatic reaction is determined in order to detect the analyte and, if desired, quantitate the amount of analyte that had been present in the sample.

Preferably, both incubations of the immunoassay formats of this invention, that is, the incubation wherein the relevant immunocomplex is formed and the incubation with the bridge receptor wherein the immunocomplexes are pulled out of solution and noncovalently bound to the solid phase, occur within a reaction vessel to which the first receptor is bound.

Alternatively, other preferred embodiments for the above-outlined formats for sandwich and competitive immunoassays of this invention comprise a capture system wherein FITC or another hapten, generally conjugated to a carrier protein, is bound to the solid phase to serve as the first receptor; wherein the bridge receptor (second receptor) is an antibody raised against the same hapten as that bound to the solid phase and conjugated to one member of a specific binding pair, preferably biotin and avidin or streptavidin; and wherein the third receptor to the sample analyte is conjugated to the other member of the specific binding pair, preferably avidin or streptavidin wherein the bridge receptor is biotinylated, or conversely, conjugated to biotin wherein the bridge receptor is conjugated to avidin or streptavidin.

Other preferred embodiments for the above-outlined formats for the immunoassays of this invention comprise a capture system wherein an antibody to a hapten, preferably FITC, is bound to the solid phase; wherein the bridge receptor is the hapten against which the first receptor is directed, complexed with one member of a specific binding pair, preferably a biotinylated version of the hapten, preferably FITC, or a complex of the hapten and avidin or streptavidin; and the sample analyte receptor is conjugated to the other member of the specific binding pair, preferably avidin or streptavidin if the bridge receptor (a hapten in this embodiment) is biotinylated, or conjugated to biotin if the bridge receptor is complexed with avidin or streptavidin. In this embodiment of the invention, it is the first receptor that is the anti-hapten antibody rather than the bridge receptor.

DETAILED DESCRIPTION

Abbreviations

The following list of abbreviations used in herein:

| | |
|---|---|
| A: | absorbance |
| Ab: | antibody |
| AP: | alkaline phosphatase |
| AH-Biotin-NHS: | aminohexanoyl-biotin-N-hydroxysuccinimide ester |
| AFP: | alphafetoprotein |
| BSA: | bovine serum albumiun |
| B:P ratio: | biotin to protein ratio |
| CEA: | carcinoembryonic antigen |
| CV: | coefficient of variance |
| °C.: | degrees centigrade |
| DNB: | dinitrobenzene |
| DNS: | 1,4-N,N-dimethylamino-naphthalene sulfonic acid |
| DMF: | dimethylformamide |
| EDTA: | ethylenediaminetetraacetic acid |
| EGFr: | epidermal growth factor receptor |
| EIA: | enzyme immunoassay |
| FITC: | fluorescein isothiocyanate |
| HABA: | 2-(4'-hydroxyazobenzene)-benzoic acid |
| HCG: | human chorionic gonadotropin |
| HIV: | human immunodeficiency virus |
| HPLC: | high pressure liquid chromatography |
| HPV: | human papilloma virus |
| HRP: | horseradish peroxidase |
| Kd: | kilodalton |
| MAb: | monoclonal antibody |
| PAb: | polyclonal antibody |
| PBS· | phosphate buffered saline |
| RPM: | revolutions per minute |
| SDS-Page: | sodium dodecyl sulfate-polyacrylamide gel electrophoresis |
| ST. DE: | standard deviance |
| tb: | tube |
| TMB: | 3,3',5,5'-tetramethylbenzidine |
| TRITC: | tetramethyl rhodamine isothiocyanate |
| Tris: | tris (hydroxymethyl) aminomethane or amino-2-hydroxy methyl-1,3-propanediol |
| TSH: | thyroid stimulating hormone |
| UGP: | urinary gonadotropin peptide |
| M: | molar |
| μg: | microgram |
| mg: | milligram |
| mL | milliliter |
| mm: | millimeter |
| ng: | nanogram |
| mM: | millimolar |
| nm: | nanometer |
| × g: | times gravity |

Figure 1A:
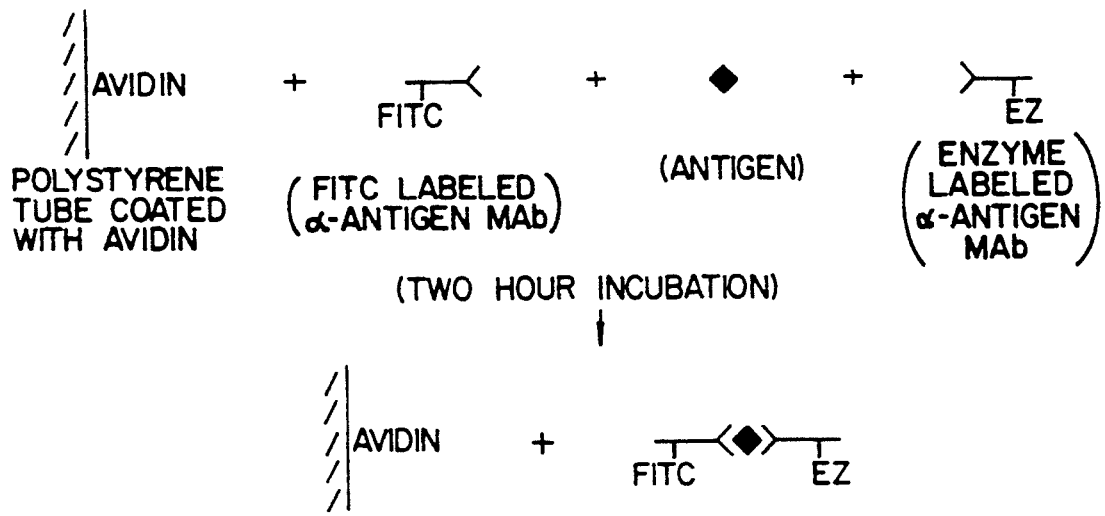
FIG. 1A–B is a schematic of a preferred embodiment of the bridge immunoassay of this invention wherein the bridge receptor is a biotinylated anti-FITC polyclonal antibody.
Figure 1B:
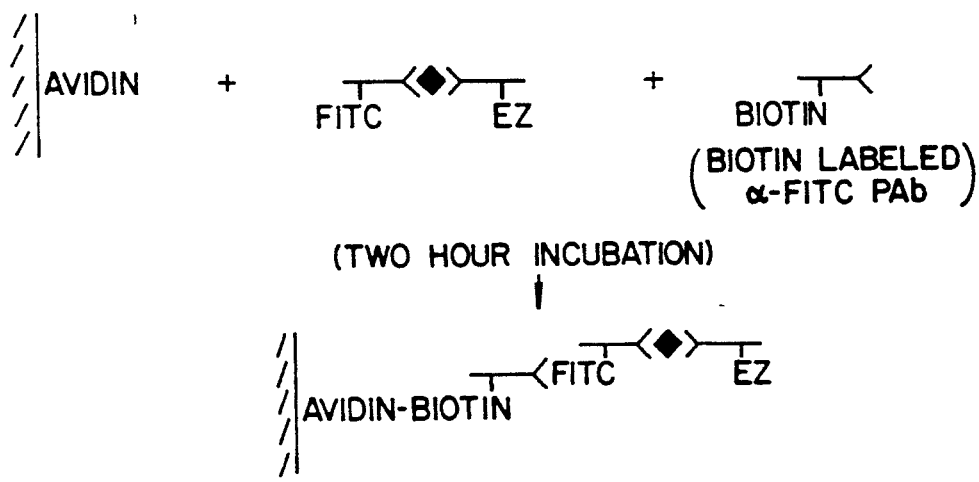

As indicated in the Summary of the Invention above, there are a variety of preferred embodiments for the triple receptor (bridge) immunoassay system of this invention. In preferred embodiments, an anti-hapten receptor, preferably an anti-hapten antibody is used. In the more preferred embodiments, the anti-hapten antibody is the bridge receptor, and still more preferably, the hapten is conjugated to a sample analyte receptor, as exemplified in FIG. 1A–B.

A hapten is a small molecule which carries an antigenic determinant but is not immunogenic until it is chemically coupled to a larger protein carrier. The hapten-carrier complex will then stimulate the formation of antibodies to both the hapten and the carrier.

A large variety of high titer, high affinity haptens are known and are suitable for use in this invention. Preferably, the haptens are small molecules with a molecular weight less than 1,000 and more preferably with a molecular weight less than 500. Exemplary substances are fluorescein, dinitrobenzene (DNB), antigenic polysaccharides, and the naphthylamines, acridines and rhodamines. Fluorescein is preferred.

The hapten can be covalently bonded to the analyte receptor via a variety of conventional linking groups. For example, in the case wherein fluorescein is the hapten, derivatives of fluorescein, such as, fluorescein isothiocyanate (FITC), dichlorotriazinyl aminofluorescein, or iodoacetyl aminofluorescein can be employed; all of such fluorescein compounds can be readily covalently bonded to proteins, the first two to the protein amino groups and the last to the sulfhydryl groups. FITC is the preferred fluoresein compound of this invention. Analogous acridine compounds also can be covalently bonded to proteins. In the case of dinitrobenzene, 2,4-dinitrofluorobenzene may be used. When using a naphthylamine as the hapten, dansyl chloride may be employed as the reactant with the receptor to form the conjugate. Also useful are rhodamine isothiocyanate, preferably tetramethyl rhodamine isothiocyanate (TRITC), and phenyl isothiocyanate.

In the case of polysaccharides, such as purified bacterial wall antigens, the covalent bonding to the receptor can be accomplished by periodate oxidation of the polysaccharide, followed by the formation and subsequent reduction of the Schiff base.

In embodiments wherein the first receptor bound to the solid phase is a hapten, and the hapten is a small molecule as, for example, FITC, TRITC, or DNB, it is preferred that such a hapten be conjugated to a carrier protein. In embodiments wherein the hapten is a peptide, for example, a peptide comprising about six to about twenty amino acids, the peptide can be coated directly to the solid phase. It may be preferable, depending upon the peptide, to attach to such a peptide hapten, a hydrophobic amino acid sequence to facilitate the binding of the peptide hapten to the solid phase.

It is also preferred that when biotin is the first receptor bound to the solid phase that it be conjugated to a carrier protein, such as, BSA or equivalent protein, because of steric considerations.

The anti-hapten receptor is preferably an antibody, either polyclonal or monoclonal, preferably monoclonal. Further, the sample analyte receptor (one in a competitive immunoassay format) or sample analyte receptors (two or more in a sandwich immunoassay format) are preferably antibodies, polyclonal or monoclonal, and more preferably monoclonal.

The techniques for making polyclonal antibodies are conventional in the immunoassay art. Also, monoclonal antibodies useful in the present invention are obtained by well known processes as described in, for example, Gulfre and Milstein, "Preparation of Monocional Antibodies: Strategies and Procedures," in *Methods in Enzymology, Immunochemical Techniques.* 73:1–46 (Langone and Vanatis eds. Academic Press 1981); and in the classic reference, Milstein and Kohler, *Nature,* 256:495–497(1975). It is preferred that wherein antibodies are used as the third and fourth receptors that they be to widely spaced epitopes on the sample analyte.

Analogously, anti-hapten antibodies are made by methods conventional in the immunoassay art. For example, the hapten may be covalently attached to bovine serum albumin (BSA) or keyhole limpet hemocyanin (KLH) or an equivalent carrier protein, and the complex is then injected into an appropriate animal to raise antibodies in accordance with well known practice.

Again, as indicated above, other organizations of the triple receptor capture system than that wherein the bridge receptor is an anti-hapten antibody and the hapten conjugated to the third receptor (a sample analyte receptor) are within the scope of this invention. The bridge separation and universal capture system are concepts that can be embodied in many combinations of receptor-ligand pairs that form a triple receptor system. Exemplary affinity ligand-receptor pairs are those in the following table. Such binding pairs are illustrative only, and the use of any other ligand-receptor combination will be obvious to those skilled in the art.

TABLE 1

| Ligand | Receptor |
|---|---|
| Antigen | Antibody |
| Hapten | Anti-hapten antibody |
| Antibody | Anti-antibody, Antigen |
| Biotin | Avidin, Streptavidin, Anti-biotin |
| Avidin | Biotin, Anti-avidin |
| Carbohydrates | Lectins |
| Dyes and hydrophobic molecules | Hydrophobic protein binding sites |
| Enzyme inhibitor, coenzyme or cofactor | Enzyme |
| Polynucleic acid | Homologous polynucleic acid sequence |
| Fluorescein | Anti-fluorescein |
| Dinitrophenol | Anti-dinitrophenol |
| Bovine serum albumin | Anti-bovine serum albumin |
| Vitamin $B_{12}$ | Intrinsic factor |
| Thyroxine | Thyroxine binding globulin |
| Cortisone, cortisol | Cortisol binding protein |
| Ligands for specific receptor protein | Membrane-associated specific receptor proteins |

The sample analyte can be an antigen, a hapten or an antibody. Exemplary antigens that are analytes that can be detected and quantified according to the immunoassay methodology of this invention include cancer antigens, such as, cathepsin D, epidermal growth factor receptor (EGFr), c-erbB-2 protein, cytokeratin, alphafetoprotein (AFP), carcinoembryonic antigen (CEA), urinary gonadotropin peptide (UGP), human chodonic gonadotropin (HCG), and other cancer marker proteins, and viral antigens, especially those associated with cancer such as human papilloma virus (HPV) antigens, hormones, such as thyroid stimulating hormone (TSH), and steroid and thyroid hormones; viruses, allergens, bacteria and toxins.

When the analyte is a hapten as, for example, a drug, a vitamin, thyroxine (T4) or an industrial pollutant or contaminant, it is preferred that the immunoassay format employed be a competitive one.

When the analyte is an antibody as, for example, an HIV antibody, preferred immunoassay formats include a variety of receptors, both antigen and/or antibody. For example, an embodiment of a sandwich immunoassay for an HIV antibody could employ the preferred generic capture system wherein the first receptor bound to the solid phase is avidin or streptavidin, and the second receptor is a biotinylated anti-hapten antibody, preferably a monoclonal antibody raised against FITC; the third receptor could be an HIV viral antigen to which the antibody under assay binds and to which FITC is conjugated; the fourth receptor of the sandwich could be either a labeled viral antigen or anti-human antibody, for example an IgG or IgM raised in a goat or a mouse, that is labeled, for example, enzymatically. Depending on the size of the antigen involved, considerations associated with steric hindrance may direct the assay to a format wherein the labeled anti-human antibodies are the preferred fourth receptor.

In a preferred competitive assay format for an antibody, such as, an HIV antibody, the preferred generic capture system as outlined above for the first and second receptors could be used; the third receptor could be preferably a viral antigen to which the antibody under assay binds or an anti-antibody to the antibody under assay and to which of either embodiment components the hapten FITC is conjugated; and the unlabeled antibody under assay could compete for binding with a labeled analogue of such antibody which is provided at a known concentration.

A still further embodiment of such an immunoassay of this invention for a sample antibody could be in a competitive/sandwich format. Again the generic capture system of the first and second receptors as outlined above could be preferably used; the third receptor could preferably be an antibody to an antigen to which the antibody under assay binds and to which the hapten FITC is conjugated; an additional component of the bridge assay in this embodiment would be said antigen (which could be termed a fourth receptor, acting as an analyte receptor) to which both the antibody under assay and a labeled antibody analogue provided at a known concentration bind. The antibody under assay can compete for binding to the antigen with either the third receptor (hapten conjugated antibody) or the analogue antibody or both. A determination concerning the presence or amount of the antibody under assay can be made by analyzing the results of the competitive binding wherein the presence of label immobilized upon the solid phase is inversely proportional to the concentration of the antibody under assay. Exemplary antigens useful to detect HIV antibodies in the bridge immunoassay formats of this invention include the following: genetically engineered HIV1 antigens corresponding to HIV1 -gp41 (gp41-recombinant, Centocor TM -p121) and HIV1 -p24 (p24-recombinant, Centocor TM -pg2) chemically synthesized peptides of HIV1-gp41 (gp41-peptides, Wang et al., *PNAS,* 83:6159 (1986) and HIV2-gp32 (gp32-peptides, Gnann et al., *Science,* 237:1346 (1987). In alternative bridge assay formats of this invention, antigens can be labeled with biotin as described in Leary et al., *PNAS,* 80:4045 (1983).

The label used in any of the immunoassays of this invention can be any label conventionally used, for example, enzymatic, radioactive, fluorescent, bioluminescent, chemiluminescent labels or other tags such as a stable free radical, a dye or an enzyme substrate or any other known label. Preferred radioactive labels $^{125}$I and $^{57}$Co. A more preferred label is enzymatic, and still more preferred is horseradish peroxidase (HRP) which develops color upon addition of the enzyme substrate, which, in the case of HRP, is a solution of hydrogen peroxide and 3, 3', 5, 5'- tetramethylbenzidine-2HCI (TMB). Other preferred enzymatic labels include alkaline phosphatase (AP) and urease.

The solid phase used in the immunoassay bridge separation system of this invention can be particles, beads, the walls or wall coatings on the reaction vessel, or an insert, preferably of large surface area placed into the reaction vessel. Preferably, the solid phase is the internal surface of the reaction vessel, more preferably the internal surface of a plastic tube, preferably a polystyrene test tube.

The sample can be any fluid containing the analyte. In preferred embodiments of the invention, the fluid is serum or a tissue extract. The fluid can be urine; however, when biotin is a component of the assay system, for example, wherein the bridge receptor is an anti-hapten biotinylated bridge antibody, and the sample fluid is urine, it is important to pre-treat the urine sample before performing the assay to remove endogenous biotin that can interfere with accurate quantification of the sample analyte.

The following sections provide illustrative means of optimizing the components of representative embodiments of the bridge immunoassay methodology of this invention. The sections are primarily directed to the preferred embodiment of the invention as illustrated in FIG. 1 and its variation wherein the bridge receptor is a biotinylated anti-FITC monoclonal antibody, but those skilled in the art understand that analogous procedures can be used to optimize the components of other bridge immunoassay embodiments of this invention.

Optimizing Amount of First Receptor

Figure 2:
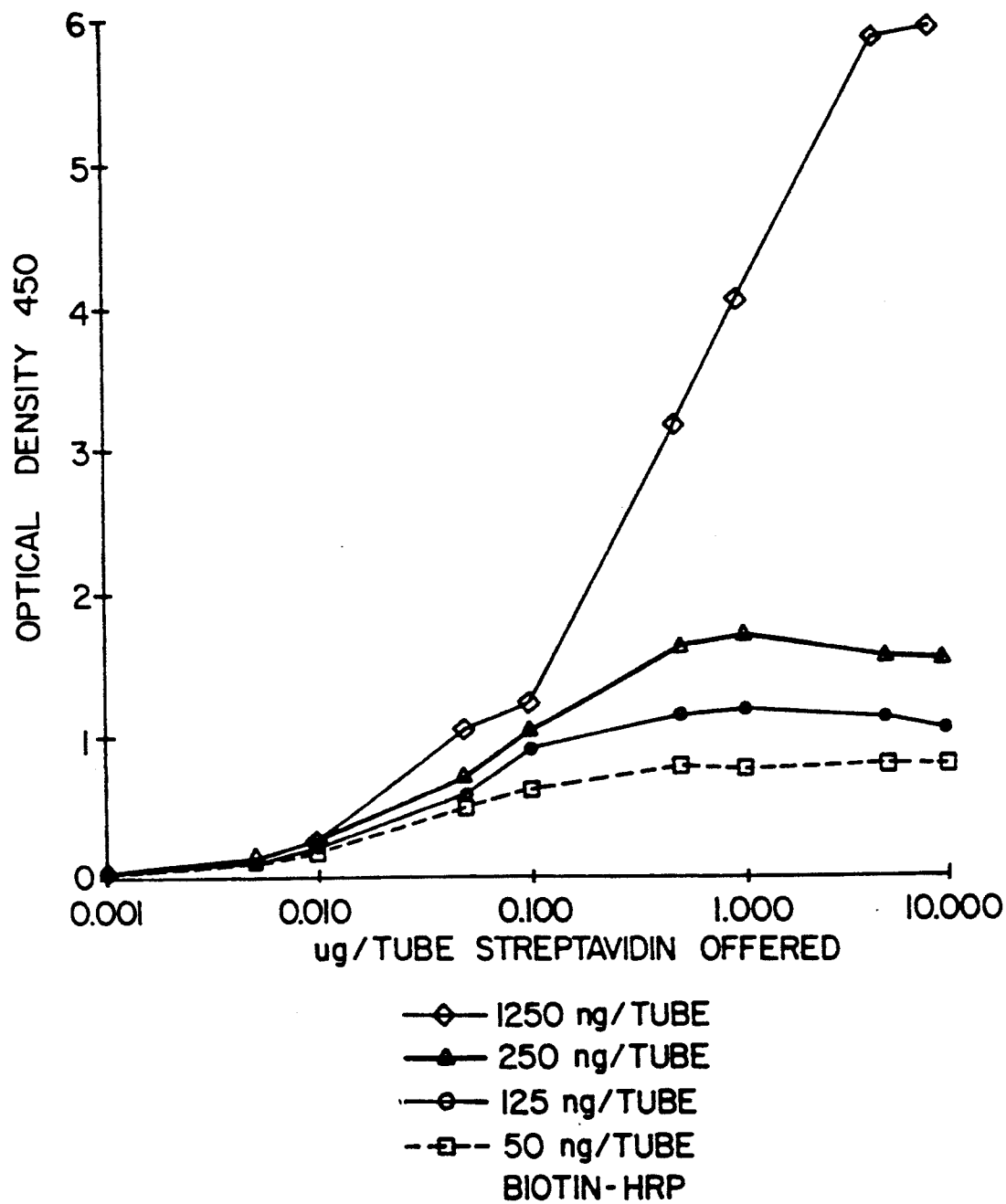
FIG. 2 is a graph used to optimize the concentration of a first receptor, in this case, streptavidin, immobilized to a solid phase.

Test methods can be established for determining the optimal amount of the first receptor bound to the solid phase for a particular reaction volume and vessel. For example, in a preferred embodiment wherein the first receptor is streptavidin (Zymed Laboratories, South San Francisco, Calif. (USA); catalog #43-4301) coated to the inner walls of polystyrene test tubes (12 mm × 75 mm; Nunc star tubes; Nunc, Napierville, Ill. (USA); catalog #47031 9) and wherein the reaction volume is 0.5 mL, it was determined that near maximum binding of a biotinylated species to the streptavidin was insured when the tubes were coated with 2.5 $\mu$g/tube of streptavidin. To reach that conclusion, various quantities of streptavidin, from 0 to 10 $\mu$g per tube were coated to the inner walls of the polystryene tubes according to the coating procedures outlined in Example 1 below, and the bound streptavidin was reacted with biotinylated - HRP. After washing, the color obtained upon the addition of a TMB substrate after a two-minute incubation time is proportional to the binding capacity of streptavidin coated onto the tube. As can be seen in FIG. 2, the binding capacity of streptavidin increases until it attains a maximum at 1 $\mu$g/tube and then plateaus for levels of the biotinylated species within the standard curve range. To insure maximum binding, the tubes for this preferred embodiment are coated with 2.5 $\mu$g per tube of steptavidin.

The binding of Avidin DX (Vector Laboratories, Burlingame, Calif. (USA); catalog #A-3001) to tubes was also investigated and was similar to streptavidin, the binding capacity increasing until 1 $\mu$g/tube and then plateauing. The streptavidin coating is preferred as it gave higher specific binding.

Figure 3:
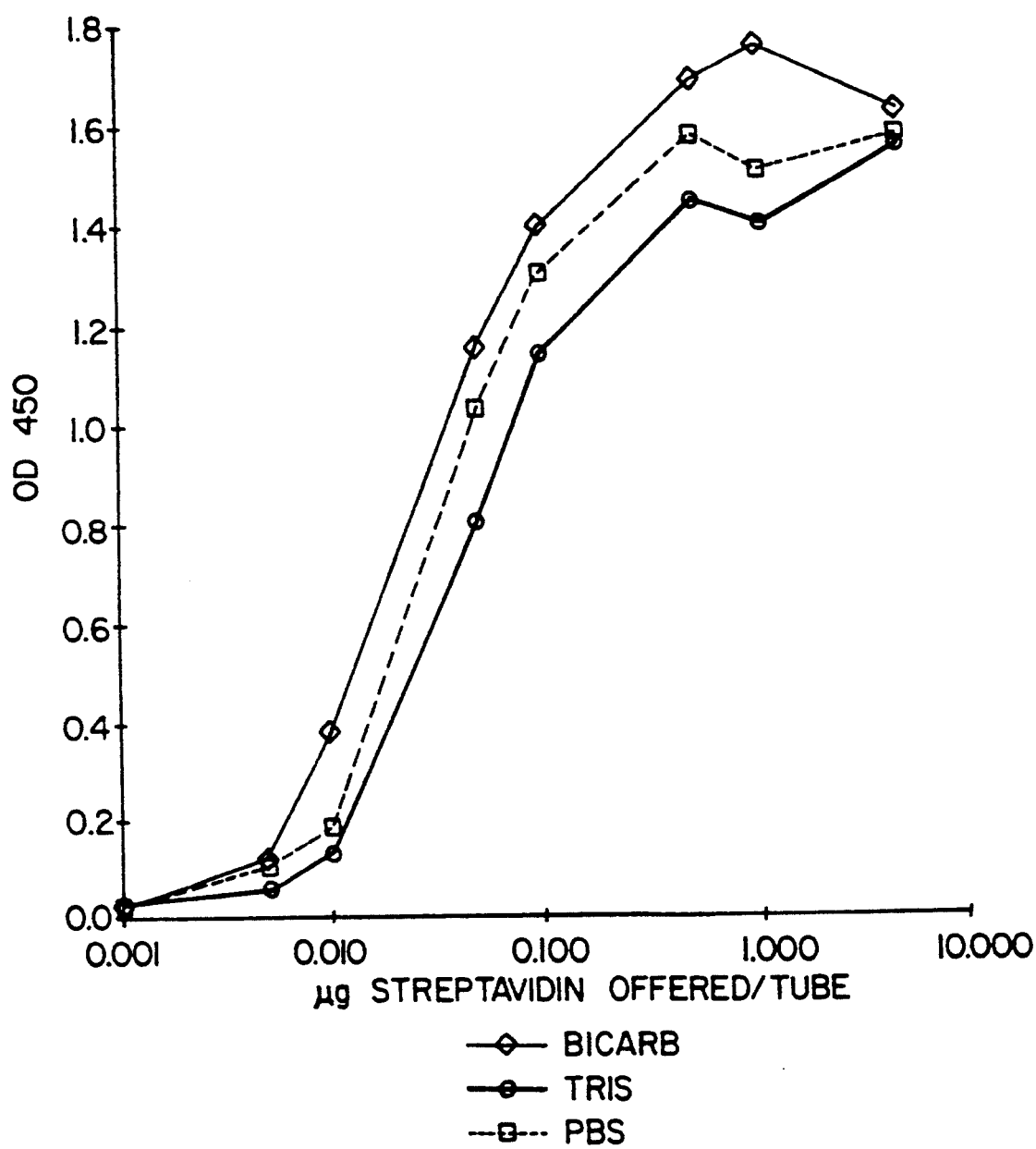
FIG. 3 is a graph used to determine a preferred coating buffer for immobilizing a first receptor, in this case, streptavidin, onto a solid phase.

For the streptavidin coating procedures of the above-identified preferred embodiment, three different buffers were investigated: 10 mM PBS pH 7.0; 50 mM Tris pH 8.5; and 50 mM sodium bicarbonate pH 9.6. As FIG. 3 indicates, the sodium bicarbonate solution gave the highest optical signal and therefore is the preferred coating buffer.

Optimizing Bridge Receptor

Test methods can also be established for optimizing the amount of the bridge receptor. For the preferred embodiment wherein the first receptor is streptavidin, wherein the reaction vessel is a polystryene tube (1 2mm ×75 mm; Nunc star tube) and the reaction volume is about 0.5 mL, and wherein the bridge receptor is a biotinylated anti-FITC polyclonal, the optimum concentration of the biotinylated antibody as well as the optimum concentration of biotin that could be conjugated to the antibody was determined. In this embodiment, the bridge receptor was a sheep anti-FITC polyclonal produced using KLH-FITC as the immunogen. The serum was purified by precipitation in 40% saturated ammonium sulphate. Purity was greater than 90% by SDS-PAGE.

A two-way optimization protocol was employed: The initial weight to weight of biotin (AH-Biotin-NHS; Zymed catalog #00-4302) to antibody was varied from 1:10 to 1:50 while the concentration of final biotinylated material was varied from 10 to 1000 ng/tube. The optimum capacity was determined using a trace amount (1 ng/tube) of FITC-HRP. A trace amount of FITC-HRP was used in order to see the signal decreasing once the optimum amount of the bridge receptor had been added. The tubes were washed, incubated with substrate (TMB), and then read in a spectrophotometer. Table 2 shows an example of typical results obtained.

TABLE 2

| | Two Way Optimization for Sheep Anti-FITC Polyclonal Antibody | | | | | | |
|---|---|---|---|---|---|---|---|
| Biotin/AB by weight | 10 ng/ tube | 50 ng/ tube | 100 ng/ tube | 200 ng/ tube | 400 ng/ tube | 800 ng/ tube | 1000 ng/ tube |
| 1/10 | 0.20 A | 0.92 A | 1.28 A | 1.35 A | 1.43 A | 1.25 A | 0.98 A |
| 1/20 | 0.35 A | 1.16 A | 1.40 A | 1.58 A | 1.43 A | 1.02 A | 0.81 A |

TABLE 2-continued

| | Two Way Optimization for Sheep Anti-FITC Polyclonal Antibody | | | | | | |
|---|---|---|---|---|---|---|---|
| Biotin/AB by weight | 10 ng/ tube | 50 ng/ tube | 100 ng/ tube | 200 ng/ tube | 400 ng/ tube | 800 ng/ tube | 1000 ng/ tube |
| 1/50 | 0.30 A | 0.99 A | 1.28 A | 1.40 A | 1.33 A | 1.17 A | 1.04 A |

Table 2 presents the absorbance values obtained for a two way optimization for the bridge polyclonal antibody. The values represent means of duplicate results. The optimization of the bridge polyclonal antibody was repeated eight times. The results consistently indicated that the optimum concentration of the bridge polyclonal antibody occurs in the range of from about 1 00 ng to about 400 ng per tube.

An initial weight: weight of 1:20 (biotin to antibody) and an assay concentration of 200 to 400 ng/tube of biotinylated polyclonal antibody can be preferably used. If 400 ng of the bridging polyclonal per tube is used, care must be used to insure that excess bridge polyclonal antibody (>400 ng) does not overwhelm the capacity of streptavidin on the tube and thereby reduce the signal.

The antibody concentration and the biotin to protein molar ratio of the bridge antibody is obtained by determining the ability of the conjugated material to bind HABA-Avidin (Harmer and Samuel, *J. Immunol. Methods*, 122:115-122 (1989)).

Still further preferred is an embodiment wherein the bridge receptor is a biotinylated anti-FITC monoclonal antibody. The monoclonal raised against KLH-FITC was prepared according to conventional procedures and purified by HPLC. Experiments were performed to find the optimum concentration for the bridge monoclonal for the same parameters as for the bridge polyclonal antibody as indicated above. Table 3 shows the signal at various concentrations of bridge monoclonal antibody.

TABLE 3

| Signal at Various Concentrations of Bridge Monoclonal Antibody | | | | | | |
|---|---|---|---|---|---|---|
| B:P Ratio | 100 ng | 200 ng | 400 ng | 600 ng | 800 ng | 1000 ng |
| 8.30 | 0.861 | 1.410 | 1.743 | 1.865 | 1.978 | 1.993 |
| 7.46 | 0.691 | 1.244 | 1.773 | 2.195 | 2.460 | 2.660 |
| 9.40 | 1.219 | 1.701 | 2.134 | 2.393 | 2.493 | 2.558 |
| 9.42 | 1.214 | 0.711 | 2.048 | 2.271 | 2.356 | 2.610 |

Table 3 shows that the signal rises rapidly as the amount of bridge monoclonal antibody is increased from 100 ng per tube, and begins to plateau at about 600 ng/tube and remains relatively level from about 800 ng/tube to about 1000 ng/tube. Thus, it was determined that a concentration of about 800 ng/tube of the biotinylated bridge monoclonal antibody was preferred.

Table 4 is an expanded version of Table 3 wherein the absorbances were converted to percentages of the 800 ng/tube value for internal consistency.

Table 4 shows that the biotinylation process is reproducible (biotin to protein ratios or B:P ratios ranging from 6.6 to about 10), and that concentrations of biotinylated bridge monoclonal antibody that are 10% or 20% more or less than the preferred 800 ng/tube do not affect the signal by more than a few percentage points.

Optimizing the Third Receptor

The amount of the third receptor (capture receptor for the analyte, preferably hapten conjugated) is proportional to the amount of the bridge receptor. In general, it is preferred that there be more bridge receptor than capture receptor. For example, in the preferred embodiment detailed above wherein a polystyrene tube is coated with streptavidin and a biotinylated anti-FITC polyclonal antibody is the bridge receptor, the amount of an FITC-conjugated capture antibody that can be used in the assay is proportional to the amount of bridge antibody that can be bound to the tube as shown in Table 2. The tube capacity for streptavidin in this preferred embodiment reaches a plateau at concentrations at or above 2.5 µg/tube. The bridge antibody that can be bound to the tube is, in turn, limited by the amount of streptavidin that has been adsorbed on the tube. However, in some instances, for example, when there is a large amount of analyte, and it is necessary to desensitize the assay, it may be preferable to decrease the amount of bridge receptor used.

Figure 4:
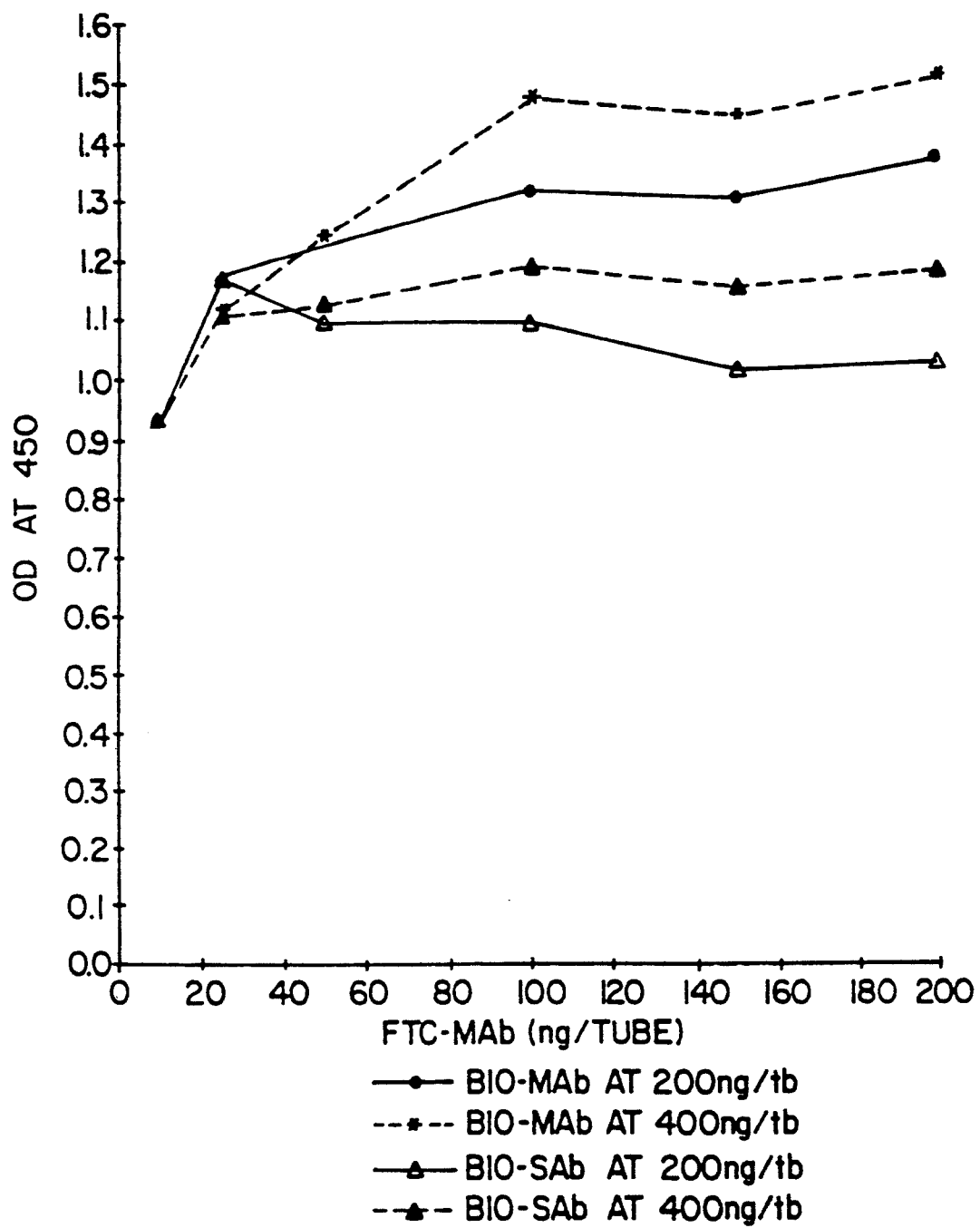
FIG. 4 graphically illustrates the effect of increasing the third receptor (hapten-conjugated monoclonal antibody as the capture antibody in this case) on different concentrations of the bridge monoclonal or polyclonal antibody (second receptor).

FIG. 4 shows the effect of increasing the amount of capture antibody, in this embodiment FITC-conjugated anti-c-erbB-2 monoclonal antibody, on different concentrations of bridge antibody (wherein "Bio-MAb" is the monoclonal bridge antibody; "Bio-SAb" is the biotinylated sheep polyclonal bridge antibody; and "FTC-MAB" is the FITC-conjugated capture monoclonal antibody for c-erbB-2). That figure shows that the bridge monoclonal works as well or better than the bridge polyclonal in a titration of the c-erbB-2 capture antibody. At least 200 ng/tube of the c-erB-2 capture antibody can be used without exceeding the capacity of the bridge antibody to link the immunocomplex to the coated tube.

In the particular preferred embodiment wherein the bridge receptor is a biotinylated anti-FITC monoclonal antibody, it is preferred that about one to about 20 times more bridge antibody be used than capture antibody, more preferably that range is from about 4 to about 12 times more bridge antibody than capture antibody on a molar basis. However, use of ratios of bridge/capture

TABLE 4

| | Percent of Signal as Compared with 800 ng Bridge/Tube | | | | | | | | |
|---|---|---|---|---|---|---|---|---|---|
| B:P Ratio | 100 ng | 200 ng | 400 ng | 600 ng | 800 ng | 1000 ng | 1200 ng | 1600 ng | 2000 ng |
| 7.70 | 70% | 86% | 103% | | 100% | 104% | | | |
| 6.60 | 65% | 86% | 100% | | 100% | 107% | | | |
| 10.05 | 62% | 80% | 98% | | 100% | 106% | | | |
| 8.30 | 44% | 71% | 88% | 94% | 100% | 101% | | | |
| 7.46 | 28% | 50% | 72% | 89% | 100% | 108% | 111% | 108% | 115% |
| 9.40 | 49% | 68% | 86% | 96% | 100% | 103% | 107% | 108% | 109% |
| 9.42 | 52% | 73% | 87% | 96% | 100% | 107% | 105% | 107% | 105% | antibodies outside those ranges can be useful in that preferred immunoassay embodiment of this invention.

Optimum Assay Conditions

Optimum assay conditions for the preferred bridge immunoassay embodiments of this invention have been determined for incubation at room temperature. The substrate incubation step of the assay was investigated with and without the use of a shaker (with or without 300 RPM for a 15 minute developmental period). The results indicated that the coefficients of variance improve with the use of a mechanical shaker.

In simulated shipping tests, it was found that the use of a bichromatic filter rather than a monochromatic filter produces better coefficients of variance because it eliminates interferences due to scratches on the tubes. Thus, the use of a bichromatic filter is preferred in reading results.

It was found that DNS, KATHON or TWEEN-20 at commonly used concentrations, 1 % or 6% BSA, 1 % fetal calf serum, and 1 % normal mouse serum do not interfere with the bridge assay for c-erbB-2 when used in the reagent buffer, but that 6% BSA when used in the calibrator matrix, in addition to that used in the reagent buffer, caused a decrease in signal.

It is preferred that the streptavidin coated tubes and anti-FITC bridge antibody be maintained at from about 2° C. to about 8° C. during storage.

Stability Data

Stability data was obtained for the components of preferred embodiments of the bridge format components of this invention: streptavidin coated polystyrene tubes (12 mm×75 mm; Nunc star tubes), the biotinylated sheep anti-FITC polyclonal antibody and the biotinylated mouse anti-FITC monoclonal antibody. An Arrhenius plot of streptavidin coated tubes shows that the tubes are stable for 167 days at 4° C. Real time stability data up to day 160 shows that the tubes have retained 100% of their day0activity. It is expected that the coating will be stable up to one year.

Stability data obtained for biotinylated anti-FITC polyclonal antibody up to day 136 showed the following: stability of 93%, 93% and 83% at 25° C., 37° C. and 45° C., respectively.

Figure 5:
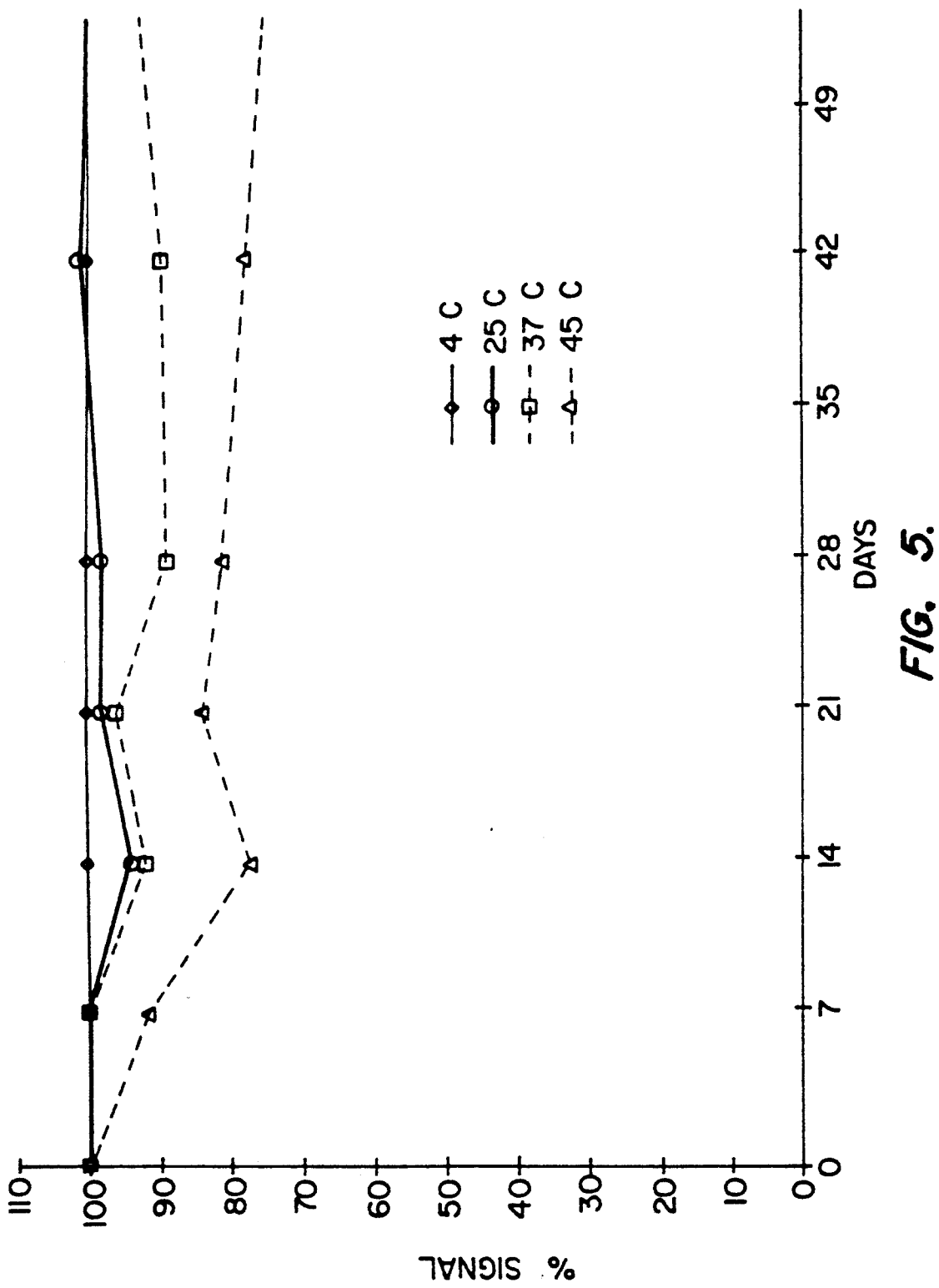
FIG. 5 graphically shows the stability over time and at various temperatures of a preferred bridge receptor of this invention, a biotinylated anti-FITC monoclonal antibody.

FIG. 5 shows that the stability of the bridge monoclonal antibody will be at least six months with one year probable.

Cross-Reactivity Studies

Therapeutic drug cross-reactivity studies were performed using the biotinylated anti-FITC monoclonal antibody (the preferred bridge receptor) to determine the amount of cross-reactivity present between the anti-FITC monoclonal and drugs which are structurally related to fluorescein. The three drugs tested were carbamazepine, chlorpromazine-HCl and thiothixene, and the observed cross-reactivity was 0.001%, 0.0025%, and 0.0033% respectively. Therefore, cross-reactivity interference was not considered to present a significant variable that could affect assay results according to this invention.

The following specific examples are intended as illustrations but not limitations on the scope of the present invention.

EXAMPLE 1

Protocol for Coating Solid Phase with Streptavidin

This example describes a representative method of binding to a solid phase a first receptor of the generic capture system of the immunoassay methodology of this invention. This example specifically describes a protocol for coating polystyrene tubes (12 mm×75 mm; Nunc star tubes; catalog #470319) with streptavidin.

To the polystyrene tubes is added one-half milliliter (mL) of streptavidin (Zymed catalog #43-4301) in a coating buffer of sodium bicarbonate at pH 9.6 at a concentration of 5 micrograms ($\mu$g) of streptavidin per milliliter (mL). The tubes are covered and stored at 2° C. to 8° C. for about 16 to 24 hours. The liquid is then aspirated from the tubes which are then washed twice with two milliliters (mL) of phosphate buffered saline (PBS)/0.05% TWEEN 20 (non-ionic detergent) wash buffer.

Two milliliters of PBS-L% bovine serum albumin (BSA) blocking solution are added to the tubes and incubated at room temperature for about 2 to 4 hours. The liquid is then aspirated from the tubes which are then washed twice with a 1% glucose solution. The liquid is then aspirated. The tubes are then uncovered and placed in a drying chamber until thoroughly dry, which usually occurs overnight. The dried tubes are then placed in a heat-sealable Mylar (moisture resistant plastic) pouch with a desiccant pack and maintained therein until ready for use in an assay procedure of this invention.

EXAMPLE 2 c-erbB-2 Serum Assay

The c-erbB-2 oncogene, also referred to as HER-2 or neu, encodes for a 185 kilodalton (Kd) protein. Studies have reported c-erbB-2 gene amplification in human mammary tumor cell lines (Kraus et al., EMBO J., 6:605-610 (1987); van de Vijver et al., *Mol. Cell Biol.*, 7:2019-2023 (1987). Also, c-erbB-2 gene amplification in human breast cancer has been shown to be associated with disease behavior, and may be a predictor of clinical outcome (Slamon et al., *Science*, 235:177-182 (1 987); Berger et al., *Cancer Res.*, 48:1238-1243 (1988); Zhou et al., *Cancer Res.*, 47:6123-6125 (1987); and Venter et al., Lancet, 11:69-71(1987).

Antibodies developed to the c-erbB-2 protein have permitted the immunohistochemical detection of the level of c-erbB-2 protein expression in fixed human tissue sections (Barnes et al., *Br. J. Cancer,* 58:448-452 (1988); Gusterson et al., *Br. J. Cancer,* 58:453-457(1988); Wright et al., *Cancer Res,* 49:2087-2090 (1989); Slamon et al., *Science,* 244: 707-712 (1989); and Tanden et al., *J. Clin. Oncol.,* 7:1120-1128 (1989 ). The expression of the c-erbB-2 protein has shown a correlation with DNA amplification (Barnes et al, ild.; Gusterson et al., 11.) Those antibodies to c-erbB-2 protein have also permitted the development of c-erbB-2 assays based on direct antigenic recognition to quantitate the c-erbB-2 protein in serum of breast cancer patients.

Thus, the quantitative measurement of the c-erbB-2 protein may have value in the prognosis of patients with diagnosed breast carcinoma. An elevated c-erbB-2 value may be associated with a poor prognosis.

c-erbB-2 Serum Enzyme Immunoassay (EIA)

The c-erbB-2 Serum Enzyme Immunoassay (EIA) described in this example is representative of the novel immunoassay methodology of this invention in a sandwich assay format. The c-erbB-2 serum EIA described in this example is a monoclonal antibody-based immunoenzymetric assay wherein mouse monoclonal antibodies against the c-erbB-2 protein conjugated to either the hapten fluorescein isothiocyanate (FITC) or the enzyme horseradish peroxidase (HRP) are both incubated with serum specimens, c-erbB-2 calibrators and c-erbB-2 control respectively in separate polystyrene tubes coated with streptavidin. During that incubation step, the c-erbB-2 protein present in the specimen, calibrators and control is bound by the FITC-conjugated monoclonal antibodies and HRP-conjugated monoclonal antibodies to form sandwich immunocomplexes.

In a second incubation, a bridge receptor, in this case, a biotinylated mouse monoclonal antibody raised against FITC, is added to the reaction mixture and acts to link the immunocomplexes to the solid phase by binding to the FITC of the FITC-conjugated monoclonal and binding on its biotinylated side to the streptavidin coating of the reaction tube. Unbound reactants are then removed by aspiration and by washing the tubes.

An enzyme substrate solution is then added to the tubes, in this case, hydrogen peroxide and 3, 3', 5, 5'-tetramethylbenzidine. 2 HCI (TMB-HCI), and incubated with the bound immunocomplexes. Phosphoric acid is then added to the tubes to stop the enzyme reaction. The intensity of the color formed by the enzyme reaction is proportional to the concentration of c-erbB-2 protein in the specimen, within the working range of the assay. The intensity of the color developed is read with a spectrophotometer set at 450 nanometers (nm).

A calibration curve is obtained by plotting the c-erbB-2 concentration of the c-erbB-2 calibrators versus absorbance. The c-erbB-2 concentration of the specimen and control, run concurrently with the calibrators, can be determined from the curve.

c-erbB-2 Serum EIA kit

A representative kit of this invention used to perform sandwich immunoassays according to the novel immunoassay methodology of this invention is described in this example. Such a representative kit to test serum samples immunoenzymetrically for the presence of c-erbB-2 protein can comprise the following components:

1. reaction vessels to which the first receptor is bound, preferably polystrene assay tubes (12 mm×75 mm) coated with streptavidin (according to Example 1);
2. sample diluent in a container, preferably a 55 mL bottle, comprising a buffer with protein stabilizer and preservative, most preferably comprising 50 mM Tris at pH 7.4; 300 mM sodium chloride; 0.1% bovine serum albumin; 0.625% normal mouse serum; 0.1% KATHON and 50 μg/ml Gentamicin sulfate;
3. c-erbB-2 calibrators in separate containers, preferably in five separate vials (0.5 mi), in a diluent comprising a buffer with protein stabilizer and preservative, at 0 units/ml, 12.5 units /mL, 25 units/ml, 50 units/ml and 100 units/ml wherein the unit value assignments are arbitrary but reflect the amount of c-erbB-2 present on a relative basis wherein assigned value is referenced to a maintained reference antigen preparation and wherein the preferred diluent comprises 50 mM Tris at pH 7.4; 150 mM sodium chloride; 1.0% bovine serum albumin; 0.8 mM EDTA; 0.1% KATHON; and 50 μg/ml Gentamicin sulfate;
4. a c-erbB-2 control at 20 units/ml in a container, preferably a vial (0.5 mi), in the same diluent as that for the calibrators (detailed immediately above);
5. enzymatically labeled and FITC-conjugated antibodies against c-erbB-2 protein, preferably monoclonal antibodies conjugated to HRP and monoclonal antibodies conjugated to FITC, in a container, preferably a bottle (20 mi), in a diluent, preferably comprising a buffer with protein stabilizer and preservative, most preferably comprising 50 mM Tris at pH 7.4; 0.1% bovine serum albumin; 0.1 mg/ml DNS; 0.05% TWEEN 20; 0.1% KATHON; and 50 μg/mi Gentamicin sulfate;
6. biotinylated bridge antibodies, preferably mouse monoclonal antibodies raised against FITC, in a container, preferably a 20 mL bottle, in a diluent, preferably comprising a buffer with protein stabilizer and preservative, more preferably comprising the same diluent as that specified for the anti-c-erbB-2 monoclonal antibodies (detailed immediately above) except without DNS;
7. washing solution concentrate in a container, preferably a 55 mL bottle, comprising a buffered detergent solution, preferably comprising 50 mM Tris at pH 7.4 and 0.05% TWEEN 20;
8. enzyme substrate, preferably TMB reagent (3, 3', 5, 5'-tetramethylbenzidine.2 HCI) solution in a container, preferably a 55 mL bottle;
9. a commercially available TMB diluent comprising a buffer containing hydrogen peroxide and preservative (TMB reagent and diluent are commercially available, sold together but in separate containers); and
10. stopping solution in a container, preferably a 1 1 0 mL bottle, comprise ng 1 M phosphoric acid.

Such a representative kit is preferably stored at a temperature range of from about 2° C. to about 8° C. The washing solution concentrate and stopping solution may be stored at a room temperature (about 15° C. to about 30° C.). The streptavidin coated assay tubes and stopping solution can be packaged and shipped separately with the other kit components. The TMB solution should not be exposed to strong light during storage or incubation nor should it be placed in contact with any oxidizing agents.

Procedure to Use c-erbB-2 Serum EIA Kit

Preparation of Washing Solution. The washing solution concentrate is brought to room temperature (from about 15° C. to about 30° C.). The washing solution concentrate is then diluted 1:40 in distilled or deionized water, mixed thoroughly and stored at 2° C. to 8° C. The diluted washing solution is used within 48 hours of preparation.

Specimen Collection and Preparation for Analysis. A blood sample is collected from a patient in a manner to avoid hemolysis, and stored immediately after collection at 2° C. to 8° C. The blood is allowed to clot and then centrifuged to separate the serum. Serum samples that appear turbid or contain particulate matter are centrifuged prior to use in the assay. If the specimen is to be tested within 24 hours, it is stored at 2° C. to 8° C., but if the testing is to be delayed more than 24 hours, it is frozen. Repeated freezing and thawing of the specimens is avoided.

Assay Procedure

Procedural Notes. All reagents and specimens are added to the lower third of the tube and are not dispensed down the side from the top of the tube. Prior to using, all reagents are gently swirled to mix. Each serum specimen, calibrator and control is assayed in duplicate each time the test is performed. The TMB solution and diluent for TMB are brought to room temperature before use. The calibrators, control and specimens are kept on ice during use.

First incubation. Two streptavidin coated assay tubes for each of the calibrators, control and each specimen to be assayed are labeled appropriately and set up in a test tube rack. Pipetted into each of the tubes is 0.20 mL of the sample diluent. Then pipetted into the appropriately labeled tubes are 0.05 mL each of the calibrator, control, and specimen. Then pipetted into all the tubes are 0.20 mL of the monoclonal antibodies against c-erbB-2 protein conjugated respectively to HRP and to FITC. The tubes are then covered and shaken gently to mix. The tubes are then incubated at room temperature (15° C. to 30° C.) for about two hours plus or minus ten minutes.

Second incubation. Then 0.20 mL of the solution containing the biotinylated bridge monoclonal antibodies raised against FITC is dispensed into all the tubes. The tubes are again covered and shaken gently to mix and incubated at room temperature (15° C. to 30° C.) for about two hours plus or minus ten minutes.

Color development. The liquid contents of each tube is then removed by aspiration, and each tube is then washed with 2 mL of the washing solution three times. After the last tube wash, the test tube rack is inverted, and the tubes are blotted onto paper towels or other suitable absorbent material For optimum performance of the assay, the washing steps are carried out thoroughly.

A TMB substrate solution is prepared by mixing equal volumes of the TMB solution and TMB diluent. Dispensed into each tube is 1.0 mL of TMB substrate solution. Timing for the color development begins with the addition of TMB substrate solution to the first tube.

The tube reactants are then incubated at room temperature for about fifteen minutes plus or minus one minute. Then added to each tube is 1.0 mL of the stopping solution in the same sequence and time intervals as in the addition of the TMB substrate solution. The blue color in the tubes changes to yellow upon addition of the stopping solution if HRP is present.

Reading absorbances. Any air bubbles in the tubes are dislodged by gently tapping the tubes, and then the absorbances for all specimens, calibrators and control are read spectrophotometrically at 450 nm within two hours of stopping the color development. The readings can be taken directly through the coated assay tubes. If a spectrophotometer with dual wavelength capability is used for direct reading, the reference wavelength is set from 600 to 650 nm.

Figure 6:
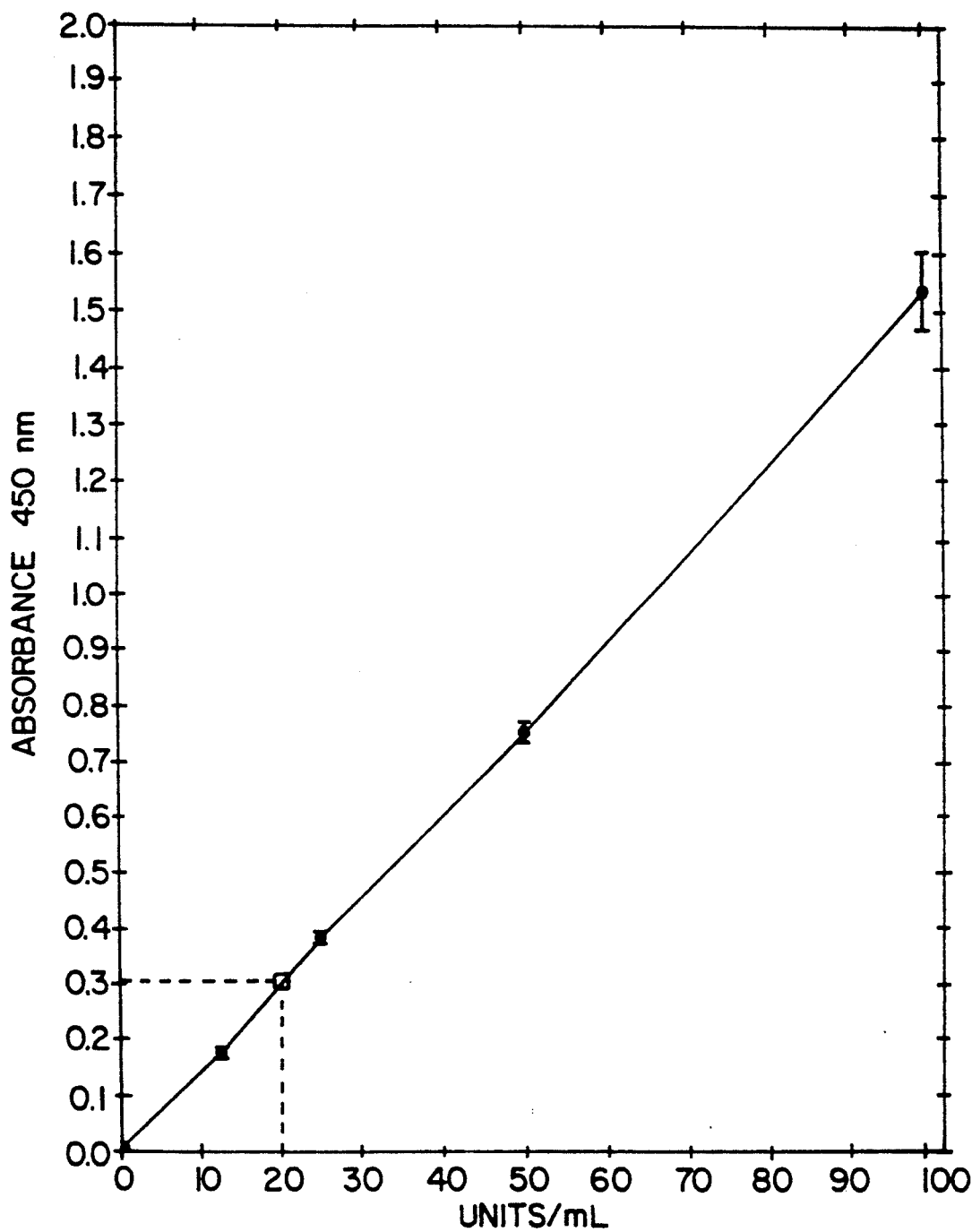
FIG. 6 is a representative calibration curve for an immunoenzymetric sandwich assay of this invention wherein the sample analyte is c-erbB-2 protein in serum.

Results. Using rectilinear graph paper, a calibration curve is constructed by plotting the average absorbance value for each c-erbB-2 calibrator on the vertical (Y) axis versus the corresponding c-erbB-2 calibrator concentration (units/mi) on the horizontal (X) axis. A representative calibration curve is shown in FIG. 6. Using the mean absorbance value obtained for each unknown specimen, the corresponding concentration of c-erbB-2 in units/ml is determined directly from the calibration curve. The c-erbB-2 value in units per mL is calculated by multiplying the c-erbB-2 concentration, as determined from the calibration curve, by the serum dilution factor. For example, if the serum specimen has been diluted 1:5 prior to being assayed, the c-erbB-2 units /mL value is multiplied by five.

Values for duplicates, except for the 0 units/ml calibrator, are not expected to differ from each other by more than 15% of the mean absorbance value. If assays in which the 0 units/ml calibrator absorbance shows an absorbance greater than 0.500 absorbance units or in which the absorbance reading for the 1 00 units/ml calibrator assay is outside of the 1.200 to 2.000 absorbance unit range, the assays are considered suspect and are repeated.

If a specimen is found to contain greater than 1 00 units/ml in an initial assay, the specimen is re-assayed according to the assay procedures described in this example, but an additional tenfold or greater dilution is performed with the appropriate amount of the sample diluent. For example, 0.05 mL of the same initial dilution of the specimen is used, and then it is diluted with 0.045 mL of the sample diluent. The assay is then repeated with the tenfold diluted specimen. Results are obtained by multiplying the value obtained from the calibration curve by the dilution factor.

Table 5 provides exemplary assay values for the c-erbB-2 serum EIA kit calibrators, control and specimens of this example.

TABLE 5

Exemplary Assay Values for c-erbB-2 Serum EIA

| Calibrator (units/mL) or Specimen | Mean Absorbance | Value from Calibration Curve (units/mL) | Multiply by Dilution Factor | c-erbB-2 (units/mL) |
|---|---|---|---|---|
| 0 | 0.004 | — | — | — |
| 12.5 | 0.176 | — | — | — |
| 25 | 0.384 | — | — | — |
| 50 | 0.757 | — | — | — |
| 100 | 1.557 | — | — | — |
| Control | 0.305 | 20.1 | — | — |
| Specimen A | 0.347 | 22.8 | 5 | 114 |
| Specimen B | >2.588 | >100 | 5 | >500 |
| Specimen B (diluted 1:50) | 0.824 | 53.4 | 50 | 2672 |

EXAMPLE 3

C-erbB-2 Serum EIA

A known amount of standard antigen was added to twenty normal human serum specimens. The assay procedures of the immediately preceding example were performed. The recovery of the added c-erbB-2 antigen from the specimens was within the range of 80.8% to 103.9%.

Known amounts of purified c-erbB-2 protein were added to a normal human serum pool and the specimens were assayed according to the above-described c-erbB-2 serum EIA procedures. The recovery of c-erB-2 from the normal human serum pool is shown in Table 6.

TABLE 6

Recovery of c-erbB-2 from Normal Human Serum Pool Using c-erbB-2 Serum EIA

| Input concentration | % Recovery |
|---|---|
| 80 | 90.5% |
| 40 | 92.3% |

EXAMPLE 4

Reproducibility of c-erbB-2 Serum EIA

Within-run reproducibility of the c-erbB-2 serum EIA of this invention as described above was measured by performing 20 replicate determinations of two different specimens in one assay. Table 7 shows the results.

TABLE 7

| Sample | Mean c-erbB-2 (units/mL) | Standard Deviation | With-in Run % (Coefficient of Variance (CV) |
|---|---|---|---|
| A | 19.6 | 1.1 | 5.6% |
| B | 72.7 | 3.5 | 4.8% |

Between-run reproducibility of the c-erbB-2 Serum EIA of this invention as described above was determined by replicate measurements of 2 specimens in 10 individually calibrated assays. Table 8 shows the results.

TABLE 8

| Sample | Mean c-erbB-2 (units/mL) | Standard Deviation | Number of assays | Between-run % Coefficient of Variance (CV) |
|---|---|---|---|---|
| A | 20.3 | 0.6 | 10 | 3.1% |
| B | 70.7 | 1.9 | 10 | 2.7% |

EXAMPLE 5 c-erbB-2 Tissue Extract EIA

This example describes a representative enzyme immunoassay of the novel immunoassay methodology of this invention wherein the analyte under assay is c-erbB-2 protein from tissue extracts. As is the c-erbB-2 serum EIA, the c-erbB-2 tissue extract EIA is preferably a monoclonal antibody-based immunoenzymetic assay using the novel capture system of this invention which in this representative preferred embodiment comprises a polystyrene tube (12mm×75mm) as the solid phase, coated with streptavidin (as the first receptor) and a biotinylated monoclonal antibody that was raised against FITC (anti-hapten bridge receptor).

The procedures for the c-erbB-2 tissue extract EIA of this invention are essentially the same as those for the c-erbB-2 serum EIA described in Example 2 except for procedural differences as pointed out below and that the specimens are prepared differently.

C-erbB-2 Tissue Extract EIA Kit

A representative kit to test tissue extract samples immunoenzymetrically for the presence of c-erbB-2 protein according to the novel immunoassay methodology of this invention comprises all the components set out in Example 2 above for the c-erbB-2 serum EIA kit and further comprises an Extraction Solution comprising buffer and detergent in a container, preferably a 55 mL bottle, wherein the preferred extraction solution comprises 50 mM Tris at pH 7.4; 1 mM EDTA; 150 mM sodium chloride; and 1 % TRITON X 1 00 (non-ionic detergent). Other differences in the two c-erbB-2 EIA kit embodiments are that the preferred containers for the calibrators and control are vials having volumes of 2.0 mL rather than 0.5 mL.

Procedure to Use c-erbB-2 Tissue Extract EIA Kit

Preparation of Washing Solution is the same as for the c-erbB-2 serum EIA.

Specimen Collection and Preparation for Analysis. Freshly excised tissue is rinsed in ice-cold physiological saline to remove excess blood. The specimen is then immediately placed in a container on ice, and fat and necrotic tissue is removed. Sample from each tissue is then histologically verified that tumor cells are present. It is important that normal or tumor-free tissue not be homogenized with tumor-rich tissue, because the protein contributed by the tumor-free tissue will result in an under-estimation of the c-erbB-2 protein content.

The tissue is then frozen to $-70°$ C. or colder using dry ice, liquid nitrogen or a $-70°$ C. freezer, and maintained at that temperature.

The tissue is then prepared by pulverizing the frozen tissue, with a pre-cooled pulverizer, or by grinding it with a mortar and pestle while it is immersed in liquid nitrogen. The tissue specimen is kept frozen during pulverization and weighing. The pulverized tissue is then transferred to a precooled, preweighed container and weighed. The weight of the tissue powder is determined to calculate the proper volumes of sample diluent and extraction solution to add to the specimen.

Cold (2° C. to 8° C.) sample diluent is added to the weighed tissue samples at a ratio of approximately 10:1 (weight to volume) for example, 2.0 mL sample diluent to 200 mg of tissue. The tissue is then homogenized taking care during the entire homogenization process to keep the tissue specimen cold. All containers used in the process are prechilled and kept in an ice bath. The tissue is then homogenized in a ultrasonic homogenizer with 5 second bursts at moderate speed. The homogenate is kept in an ice bath between bursts.

The homogenate is then centrifuged at 13,000 to 14,000 x g for 15 minutes at 4° C. in a refrigerated centrifuge or in a non-refrigerated table top microcentrifuge operated in a cold room. Most of the c-erbB-2 protein is found enriched in the pelleted material, but the supernatant may contain some activity.

After centrifugation, the supernatant is aspirated. To the pelleted material is added a volume of cold (2° C. to 8° C.) extraction solution equal to one-half the original volume of the sample diluent used for the homogenization. The pelleted material is resuspended but not completely resolubilized in the extraction solution by moderate vortexing or pipetting, while taking care to minimize foaming. The tissue extract is maintained at 2° C to 8° C.

The extract is kept on ice for 10 to 15 minutes with occasional mixing and then centrifuged at 10,000 to 14,000 x g for 15 minutes at 4° C. The supernatant is then transferred to a prechilled tube on ice.

The protein content of the extract is then determined preferably by a Pierce BCA Protein Assay (commercially available from Pierce, P.O. Box 117, Rockford, Ill., USA; Smith et al. "Measurement of protein using Bicinchoninic Acid," *Anal, Biochem.*, 12:76-85 (1985). Bovine serum albumin, or another suitable purified protein, is used to generate a standard curve. To be measured accurately against the standard curve, the tissue extract may require dilution in the sample diluent, where a dilution of approximately 1:2 or 1:5 is usually necessary. The applicable protein concentration range of the standard room temperature protocol is from about 200 µg/ml to about 1200 µg/ml. The absorbance is measured at 562 nm versus a water reference. The protein concentration of the tissue extracts is determined by interpolation from the protein standard curve.

The samples are diluted immediately prior to performing the assay. The tissue extract is adjusted to approximately 0.20 mg/ml protein concentration by adding cold (2° C. to 8° C.) sample diluent. A minimum volume of 0.20 mL of diluted tissue extract is required for each specimen assay tube.

Assay Procedure

Procedural notes are the same for both the c-erbB-2 serum and tissue extract EIAs of this invention.

First Incubation. As in Example 2, two streptavidin coated assay tubes for each of the calibrators, control and each specimen to be assayed are labeled appropriately and set up in a test tube rack. The same pipetting schedule as in Example 2 is used except that 0.20 mL rather than 0.05 mL of each calibrator, control and diluted specimen are pipetted into each of the assigned tubes. Otherwise, the first incubation is the same for both assays.

Second incubation. The second incubation is the same procedure as detailed in Example 2.

Color development is similarly the same as that described in Example 2 except that the liquid is decanted from the tubes completely for the tissue extract EIA rather than aspirated as for the serum EIA.

Figure 7:
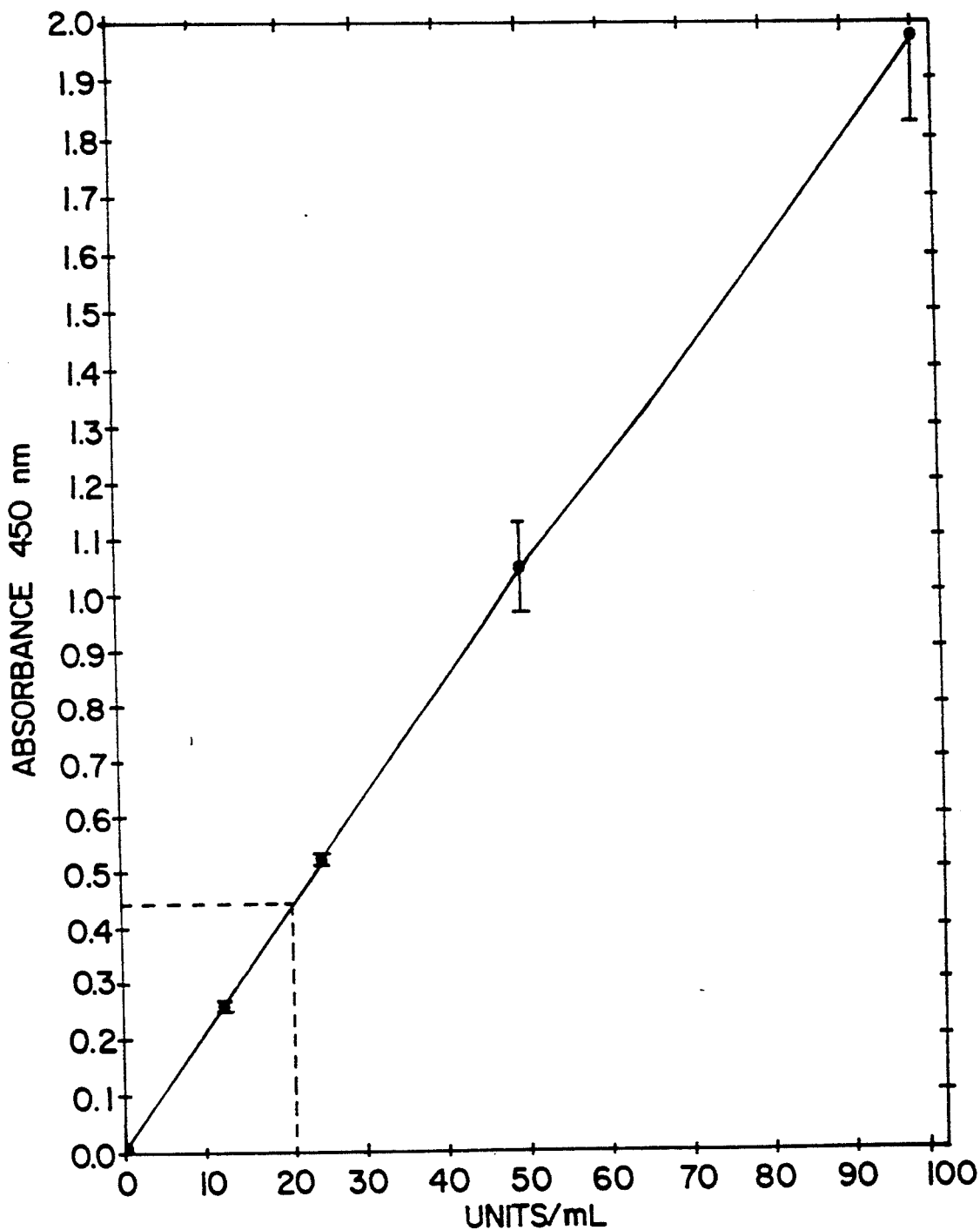
FIG. 7 is a representative calibration curve for an immunoenzymetric sandwich assay of this invention wherein the sample analyte is c-erbB-2 protein in a tissue extract.

Reading absorbances. The procedure for reading absorbances is the same as for the serum EIA of Example 2. (FIG. 7 is a representative calibration curve for the c-erbB-2 tissue extract EIA.) However, the calculation of the c-erbB-2 value in units per mg of protein is accomplished by dividing the c-erbB-2 concentration by the total protein concentration, wherein the c-erbB-2 concentration equals the value in units/mL as determined from the calibration curve. The total protein concentration equals the value in mg/ml of diluted specimen tested in the assay. For example, if the initial protein concentration of the tissue extract was 2.5 mg/ml, and the sample was diluted 1:10 prior to being assayed, the total protein concentration is 0.25 mg/ml.

As for the serum EIA, if the concentration of c-erbB-2 of a specimen is greater than 1 00 units/ml, the specimen should be re-assayed wherein an additional tenfold or greater dilution is used with the appropriate amount of sample diluent. The c-erbB-2 concentration is then calculated in units/mg as described above in this example.

Table 9 provides exemplary assay values for the c-erbB-2 Tissue Extract EIA kit calibrators, control and specimens.

TABLE 9

Exemplary Assay Values for c-erbB-2 Tissue Extract EIA

| Calibrator (units/mL) or Specimen | Mean Absorbance | Value from Calibration Curve (units/mL) | Input protein concentration | c-erbB-2 (units/mg) |
|---|---|---|---|---|
| 0 | 0.004 | — | — | — |
| 12.5 | 0.255 | — | — | — |
| 25 | 0.523 | — | — | — |
| 50 | 1.059 | — | — | — |
| 100 | 1.972 | — | — | — |
| Control | 0.443 | 21 | — | — |
| Specimen A | 0.998 | 47 | 100 | 470 |
| Specimen B | 2.592 | >100 | 100 | >1000 |
| Specimen B (diluted 1:10) | 0.570 | 27.5 | 10 | 2750 |

EXAMPLE 6 c-erbB-2 Tissue Extract EIA

Known amounts of standard antigen were added to a tumor extract negative for c-erbB-2. The assay procedures of Example 5 were performed. The recovery of the added c-erbB-2 antigen from the specimens was greater than 90%. Table 10 outlines the recovery results.

TABLE 10

Recovery of c-erbB-2 from a Tumor Extract Using c-erbB-2 Tissue Extract EIA Kit Procedure.

| Input Amount | % Recovery |
|---|---|
| 100 | 94.8% |
| 50 | 90.8% |
| 25 | 90.7% |
| 12.5 | 98.7% |

EXAMPLE 7

Reproducibility

Between-run reproducibility of the c-erbB-2 tissue extract EIA kit was determined by replicate measurements of two specimens in ten individually calibrated assays. The results are shown in Table 11.

TABLE 11

| Sample | Mean c-erbB-2 (units/mL) | Standard Deviation | Number of assays | Between-run % Coefficient of Variance (CV) |
|---|---|---|---|---|
| A | 19.3 | 0.4 | 10 | 2.3% |
| B | 73.3 | 0.8 | 10 | 1.1% |

EXAMPLE 8

Comparison of Bridge Format to Direct Format

Preferred protocols for a preferred format for a bridge sandwich immunoassay to quantitate the amount of c-erbB-2 in a fluid sample are detailed in Examples 2 and 5 above. Briefly, such a preferred bridge sandwich assay of this invention involves the addition of a FITC-conjugated capture antibody, an HRP-labeled anti-analyte antibody and a sample to streptavidin coated tubes followed by an initial incubation period of two hours after which a biotinylated anti-FITC bridge antibody is added with a second incubation of two hours. Once washed, substrate is added and incubated for 15 to 30 minutes.

Figure 8:
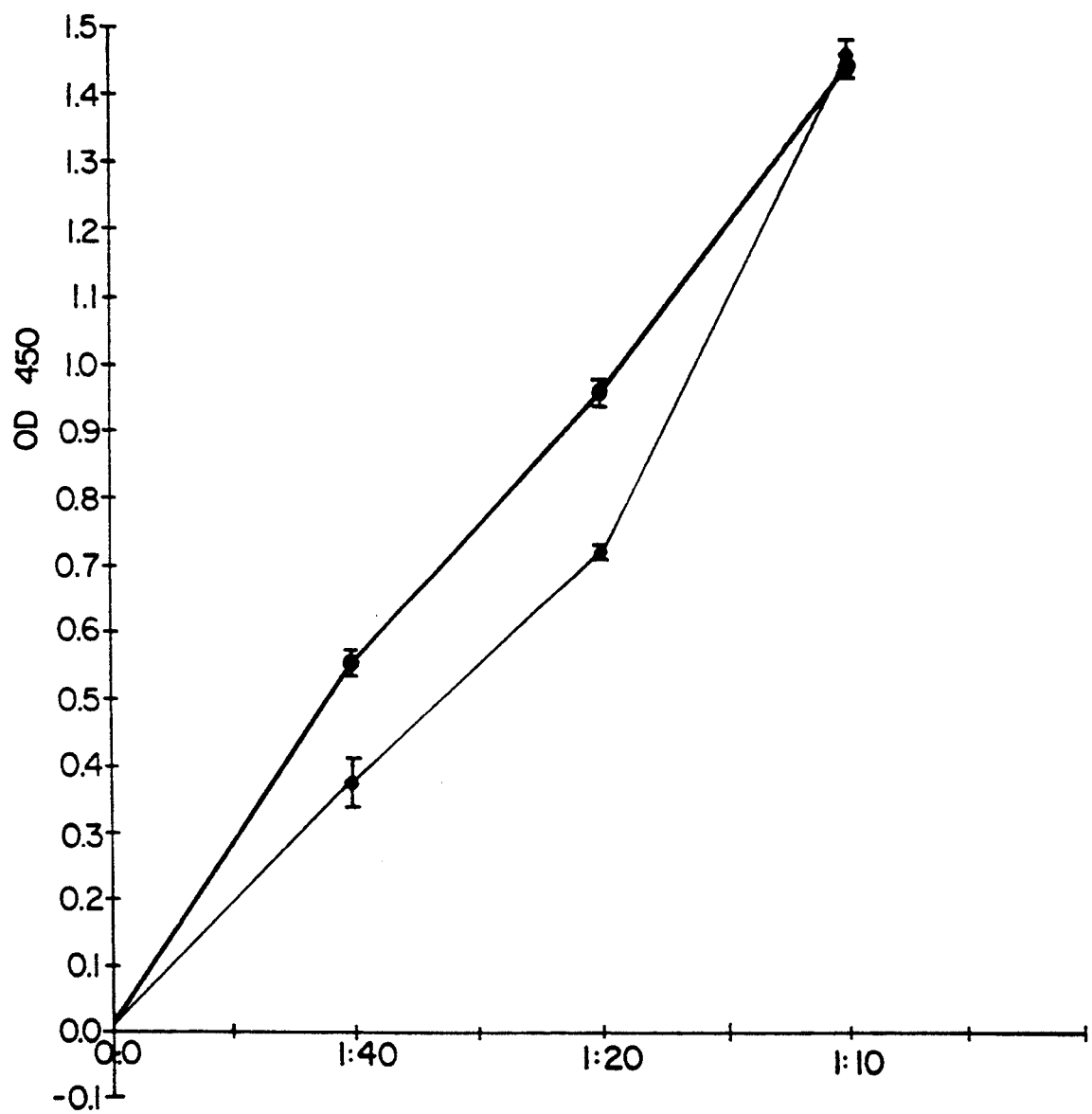
FIG. 8 graphically shows a comparison between a bridge immunoassay format of this invention and a direct assay format wherein in the latter format only an immobilized capture antibody and a labeled antibody are used. The assays were both directed to c-erbB-2 as the antigen.

Said exemplary preferred embodiment for a bridge sandwich assay of this invention was compared with a direct assay for c-erbB-2. The direct assay comprises an assay wherein only two antibodies are employed: a capture antibody to the analyte and a labeled antibody to the analyte (HRP-conjugated) wherein the capture antibody is immobilized upon a solid phase. For the comparison shown in FIG. 8, 100 ng of the capture antibody was employed per tube in the direct assay, and 400 ng/tube of the biotinylated anti-FITC monoclonal antibody for the bridge format of this invention was used. Calibrators used in both assays were not diluted on the same day. As can be seen in FIG. 8, the bridge assay response is 100% as compared to the direct assay.

Clinical data was obtained for both serum and tissue extract samples for the c-erbB-2 assays of this invention. Seventeen tissue extracts were evaluated both in the bridge assay format of this invention and in the direct assay format. A correlation of R=0.99 between the bridge and direct assay formats was obtained.

Further, 23 serum samples positive for c-erbB-2 were tested in the bridge and direct assays and a correlation of R=0.98 was obtained.

The foregoing description of the invention and the examples demonstrating its applications to assays are but representative of the various ways the invention can be utilized. That other variations will be useful will be apparent to those skilled in the art. Therefore, modifications of the above-described modes for carrying out the invention that are obvious to those of skill in the immunoassay art are intended to be within the scope of the following claims.

I claim:

1. A method of immunoassay for an analyte in a liquid sample which comprises preparing or obtaining a solid phase to which is bound a first receptor which is selected from the group consisting of avidin and streptavidin and has as its ligand biotin conjugated to a second receptor which is an anti-hapten antibody;

wherein the second receptor is a bridge receptor which has as its ligand a hapten conjugated to a third receptor;

wherein the third receptor is an antibody that is not connected to a soluble liquid matrix and has as its ligand the analyte under assay;

contacting the liquid sample containing said analyte with said third receptor in either the presence or absence of said solid phase;

linking the third receptor to the solid phase by contacting the third receptor with the bridge receptor either in the presence or in the absence of the solid phase wherein the solid phase can be introduced to the liquid sample before, after or simultaneously with the bridge receptor; and detecting and/or quantitating the analyte under assay;

wherein the molar ratio of the second receptor to the third receptor is greater than 1:1.

2. A method according to claim 1 wherein the immunoassay is in a sandwich format and further comprises contacting the liquid sample containing said analyte with a labeled fourth receptor, which is an antibody and has as its ligand the analyte under assay, before, after, or at the same time as contacting the liquid sample with said third receptor.

3. A method to claim 1 wherein the immunoassay is in a competitive format and wherein the third receptor further has as an additional ligand, a labeled analogue of the analyte under assay.

4. A method according to claim 1 wherein the hapten is selected from the group consisting of derivatives of fluorescein, dinitrobenzene, antigenic polysaccharides, naphthylamines, acridines and rhodamines.

5. A method according to claim 1 wherein the analyte under assay is an antigen, an antibody or a hapten.

6. A method according to claim 1 wherein the molar ratio of the second receptor to the third receptor is from about 4:1 to about 12:1.

7. A method according to claim 1 wherein the liquid sample is serum, a tissue extract or urine.

8. A method according to claim 2 wherein the fourth receptor is labeled with a label selected from the group consisting of enzymes, radioisotopes, stable free radicals, chemiluminescent compounds, bioluminescent compounds, fluorescent compounds, dyes and enzyme substrates.

9. A method according to claim 8 wherein the label is selected from the group consisting of enzymes, radioisotopes and dyes.

10. A method according to claim 9 wherein the label is an enzyme selected from the group consisting of horseradish peroxidase (HRP) alkaline phosphatase (AP) and urease.

11. A method according to claim 2 wherein said second, third and fourth receptors are monoclonal antibodies; and wherein said hapten is fluorescein isothiocyanate or tetramethyl rhodamine isothiocyanate.

12. A method according to claim 11 wherein the fourth receptor is a monoclonal antibody that is labeled with an enzyme selected from the group consisting of horseradish peroxidase, alkaline phosphatase (AP) and urease.

13. A method according to claim 12 wherein the liquid sample is either serum or a tissue extract and wherein the analyte under assay is c-erbB-2 protein, cytokeratin, cathepsin D or epidermal growth factor receptor (EGFr).

14. A method according to claim 3 wherein the analogue of the analyte under assay is labeled with a label selected from the group consisting of enzymes, radioisotopes, stable free radicals, chemiluminescent compounds, bioluminescent compounds, fluorescent compounds, dyes and enzyme substrates.

15. A method according to claim 14 wherein the label is selected from the group consisting of enzymes, radioisotopes and dyes.

16. A method according to claim 15 wherein the label is an enzyme selected from the group consisting of horseradish peroxidase (HRP), alkaline phosphatase (AP), and urease.

17. A method according to claim 3 wherein the second and third receptors are monoclonal antibodies.

18. A method according to claim 17 wherein the analogue is labeled with an enzyme or a radioisotope.

19. A method according to claim 4 wherein the hapten is selected from the group consisting of fluorescein isothiocyanate (FITC), tetramethyl rhodamine isothiocyanate (TRITC), dichlorotriazinyl aminofluorescein, iodoacetyl aminofluorescein, 2,4-dinitrofluorobenzene and dansyl chloride.

20. A method according to claim 19 wherein the hapten is fluorescein isothiocyanate or tetramethyl rhodamine isothiocyanate.

21. A method according to claim 20 wherein both the second and third receptors are monoclonal antibodies; and wherein the first receptor is streptavidin.

22. A method according to claim 5 wherein the analyte is an antigen.

23. A method according to claim 22 wherein the analyte is an antibody.

24. A method according to claim 23 wherein the antibody is selected from the group consisting of HIV antibodies.

25. A method according to claim 22 wherein the antigen is selected from the group consisting of c-erbB-2 protein, cytokeratin, alphafetoprotein, carcinoembryonic antigen, human chorionic gonadotropin, thyroid stimulating hormone, a steroid hormone, a thyroid hormone, a virus, an allergen, a bacterium, and a toxin.

26. A method according to claim 25 wherein the liquid sample is either serum or a tissue extract.

27. A method according to claim 5 wherein the analyte is a hapten and wherein the immunoassay is in a competitive format.

28. A method according to claim 27 wherein the hapten is selected from the group consisting of vitamins, drugs, thyroxine, and industrial contaminants and pollutants.

29. A method of immunoassay according to claim 7 wherein the liquid sample is serum or a tissue extract.

30. A method according to claim 29 wherein the liquid is urine which has been pre-treated to remove endogenous biotin.

31. A method of immunoassay for an analyte in a liquid sample which comprises preparing or obtaining a solid phase to which is bound a first receptor which is selected from the group consisting of avidin and streptavidin and which has as its ligand biotin conjugated to a second receptor which is an anti-hapten antibody;
wherein the second receptor is a bridge receptor which has as its ligand a hapten conjugated to a third receptor;
wherein the third receptor is an antibody that is not connected to a soluble liquid matrix and has as its ligand a receptor to the analyte under assay;
contacting the liquid sample containing said analyte with said third receptor;
linking the third receptor to the solid phase by contacting the third receptor with the bridge receptor either in the presence or in the absence of the solid phase wherein the solid phase can be introduced to the liquid sample before, after or simultaneously with the bridge receptor; and
detecting and/or quantitating the analyte under assay;
wherein the molar ratio of the second receptor to the third receptor is greater than 1:1.

32. A method according to claim 31 wherein the analyte is an antibody, and its receptor is an antigen to which it binds.

33. A method according to claim 31 wherein said first receptor is streptavidin; wherein said second and third receptors are monoclonal antibodies; and wherein said hapten is fluorescein isothiocyanate or tetramethyl rhodamine isothiocyanate.

34. A method of immunoassay for an analyte in a liquid sample comprising the steps of:
(a) incubating, in the presence of a solid phase to which a first receptor is bound wherein the first receptor is selected from the group consisting of avidin and streptavidin, a mixture comprising the liquid sample containing the analyte and two receptors to the analyte, one of which is labeled and one of which is conjugated to a hapten, wherein the receptor which is conjugated to a hapten is not connected to a soluble liquid matrix, for a sufficient time for sandwich immunocomplexes to form wherein said receptors are antibodies;
(b) adding to said mixture a bridge receptor which is an anti-hapten antibody which has as its ligand the hapten conjugated to said analyte receptor and to which biotin is conjugated as the ligand for the first receptor;
(c) incubating the mixture formed in step (b) for sufficient time for the immunocomplexes formed in step (a) to be immobilized upon the solid phase; and
(d) determining the amount of label that has been immobilized upon the solid phase or remains in the liquid sample and, therefrom the amount of analyte that had been present in the sample;
wherein the molar ratio of the second receptor to the third receptor is greater than 1:1.

35. A method according to claim 34 wherein the solid phase is the inner walls of a reaction vessel;
wherein the labeled analyte receptor is labeled with an enzyme;
and wherein the hapten conjugated to the other analyte receptor is a fluorescein derivative or a rhodamine isothiocyanate; and wherein the liquid sample is serum or a tissue extract.

36. A method according to claim 35 wherein step (d) comprises the following steps:
washing away excess reagent and sample and adding a substrate for the enzyme and incubating for a sufficient time for a detectable enzymatic product to form;
adding a stopping solution to the reaction vessel containing the substrate and immobilized immunocomplex; and
determining the amount of enzymatic product formed which is proportional to the amount of analyte that had been present in the sample.

37. A method according to claim 34 wherein said two analyte receptors are monoclonal antibodies; wherein said first receptor is streptavidin; and wherein said hapten is fluorescein isothiocyanate or tetramethyl rhodamine isothiocyanate.

38. A method of immunoassay for an analyte in a liquid sample comprising the steps of:
(a) incubating, in the presence of a solid phase to which a first receptor is bound, wherein the first receptor is selected from the group consisting of avidin and streptavidin, a mixture comprising the liquid sample containing the analyte, a labeled analogue of the analyte provided at a known concentration, and a receptor to the analyte which is conjugated to a hapten, wherein the receptor which is conjugated to a hapten is not connected to a soluble liquid matrix, for a time sufficient for immunocomplexes to form comprising the analyte receptor and either the analyte or the labeled analogue of the analyte wherein said hapten conjugated analyte receptor is an antibody;
(b) adding to said mixture a bridge receptor which is an anti-hapten antibody and has as its ligand the hapten conjugated to said analyte receptor, and to which biotin is conjugated as the ligand for the first receptor;
(c) incubating the mixture formed in step (b) for sufficient time for the immunocomplexes formed in step (a) to be immobilized upon the solid phase; and
(d) determining the amount of label that has been immobilized upon the solid phase or remains in the liquid sample and, therefrom the amount of analyte that had been present in the sample;
wherein the molar ratio of said bridge receptor to said analyte receptor is greater than 1:1.

39. A method according to claim 38 wherein said first receptor is straptavidin; wherein said analyte and bridge receptors are monoclonal antibodies; and wherein said hapten is a fluorescein derivative.

40. A diagnostic kit for an analyte comprising:
(a) a solid phase coasted with a first receptor selected from the group consisting of avidin and streptavidin;

(b) a container containing two receptors to the analyte to be assayed, one of which is labeled and the other of which is conjugated to a hapten, wherein the receptor which is conjugated to a hapten is not connected to a soluble liquid matrix, and wherein said receptors are antibodies; and (c) a container containing a bridge receptor which is an anti-hapten antibody which has as its ligand the hapten conjugated to said analyte receptor, and to which biotin is conjugated as the ligand for the first receptor;

wherein the molar ratio of said bridge receptor to said hapten-conjugated analyte receptor is greater than 1:1.

41. A diagnostic kit according to claim 40 wherein said first receptor is streptavidin;

wherein said two analyte receptors and bridge receptor are monoclonal antibodies; and wherein said hapten is fluorescein isothiocyanate or tetramethyl rhodamine isothiocyanate.

* * * * *